(12) United States Patent
Magar et al.

(10) Patent No.: US 8,926,509 B2
(45) Date of Patent: Jan. 6, 2015

(54) WIRELESS PHYSIOLOGICAL SENSOR PATCHES AND SYSTEMS

(75) Inventors: Surendar Magar, Dublin, CA (US); Venkateswara Rao Sattiraju, Union City, CA (US); Ali Niknejad, Berkeley, CA (US); Louis Yun, Los Altos, CA (US); James C. Beck, Berkeley, CA (US)

(73) Assignee: Hmicro, Inc., Fremont, CA (US)

( * ) Notice: Subject to any disclaimer, the term of this patent is extended or adjusted under 35 U.S.C. 154(b) by 605 days.

(21) Appl. No.: 12/134,151

(22) Filed: Jun. 5, 2008

(65) Prior Publication Data

US 2009/0054737 A1 Feb. 26, 2009

Related U.S. Application Data

(60) Provisional application No. 60/968,023, filed on Aug. 24, 2007.

(51) Int. Cl.
*A61B 5/00* (2006.01)
*A61B 5/0205* (2006.01)
(Continued)

(52) U.S. Cl.
CPC .............. *A61B 5/0205* (2013.01); *A61B 5/0024* (2013.01); *A61B 5/0404* (2013.01);
(Continued)

(58) Field of Classification Search
CPC ............... H04W 84/005; H04W 84/18–84/20; H04W 88/08–88/10; H04W 52/0203–52/0206; H04W 52/0209; H04W 52/0212; H04W 52/0261–52/0296; A61B 5/0024; A61B 5/6801; A61B 5/0002; A61B 5/7221; G06F 19/3418; H04L 67/125; H04L 67/04

See application file for complete search history.

(56) References Cited

U.S. PATENT DOCUMENTS

| 4,313,443 A | 2/1982 | Frosch et al. |
| 4,784,162 A | 11/1988 | Ricks et al. |

(Continued)

FOREIGN PATENT DOCUMENTS

| EP | 1070479 A2 | 1/2001 |
| EP | 1292218 B1 | 4/2006 |

(Continued)

OTHER PUBLICATIONS

Montemont, G. et al in "Experimental Comparison of Discrete and CMOS Charge Sensitive Preamplifiers for CZT Radiation Detectors", IEEE Transactions on Nuclear Science, vol. 50, No. 4, 2002, p. 936-941.*

(Continued)

*Primary Examiner* — William Thomson
*Assistant Examiner* — Marie Archer
(74) *Attorney, Agent, or Firm* — Wilson Sonsini Goodrich & Rosati

(57) ABSTRACT

The present invention provides methods, devices, and systems for wireless physiological sensor patches and systems which incorporate these patches. The systems and methods utilize a structure where the processing is distributed asymmetrically on the two or more types of ASIC chips that are designed to work together. The invention also relates to systems comprising two or more ASIC chips designed for use in physiological sensing wherein the ASIC chips are designed to work together to achieve high wireless link reliability/security, low power dissipation, compactness, low cost and support a variety of sensors for sensing various physiological parameters.

31 Claims, 10 Drawing Sheets

(51) Int. Cl.
*A61B 5/0404* (2006.01)
*A61B 5/11* (2006.01)
*H04L 29/08* (2006.01)
*G06F 19/00* (2011.01)
*H04W 88/00* (2009.01)
*H04W 52/00* (2009.01)
*H04W 84/00* (2009.01)
*A61B 5/021* (2006.01)
*A61B 5/024* (2006.01)
*A61B 5/0476* (2006.01)
*A61B 5/0488* (2006.01)
*A61B 5/145* (2006.01)

(52) U.S. Cl.
CPC ............ *A61B 5/1112* (2013.01); *A61B 5/6833* (2013.01); *G06F 19/3418* (2013.01); *H04L 67/125* (2013.01); *H04L 67/04* (2013.01); *A61B 5/021* (2013.01); *A61B 5/02438* (2013.01); *A61B 5/0476* (2013.01); *A61B 5/0488* (2013.01); *A61B 5/14532* (2013.01); *A61B 5/7232* (2013.01); *A61B 2560/0209* (2013.01)
USPC .......... 600/301; 600/300; 600/382; 600/391; 600/393; 700/2; 700/3; 709/208; 709/217; 709/224; 709/225; 340/539.12

(56) References Cited

U.S. PATENT DOCUMENTS

| | | |
|---|---|---|
| 5,124,128 A | 6/1992 | Hildenbrand et al. |
| 5,231,990 A * | 8/1993 | Gauglitz .................... 600/510 |
| 5,511,553 A | 4/1996 | Segalowitz |
| 5,717,848 A | 2/1998 | Watanabe et al. |
| 5,720,770 A | 2/1998 | Nappholz et al. |
| 5,913,727 A | 6/1999 | Ahdoot |
| 5,957,854 A | 9/1999 | Besson et al. |
| D439,981 S | 4/2001 | Kasabach et al. |
| 6,230,970 B1 | 5/2001 | Walsh et al. |
| 6,275,143 B1 | 8/2001 | Stobbe |
| 6,278,499 B1 | 8/2001 | Darbee et al. |
| 6,295,461 B1 * | 9/2001 | Palmer et al. ............... 455/557 |
| D451,604 S | 12/2001 | Kasabach et al. |
| 6,336,900 B1 | 1/2002 | Alleckson et al. |
| D460,971 S | 7/2002 | Sica et al. |
| 6,436,058 B1 | 8/2002 | Krahner et al. |
| 6,454,708 B1 | 9/2002 | Ferguson et al. |
| 6,463,039 B1 | 10/2002 | Ricci et al. |
| 6,494,829 B1 * | 12/2002 | New et al. ................... 600/300 |
| 6,527,711 B1 | 3/2003 | Stivoric et al. |
| 6,595,929 B2 | 7/2003 | Stivoric et al. |
| 6,605,038 B1 | 8/2003 | Teller et al. |
| 6,677,852 B1 | 1/2004 | Landt |
| 6,694,180 B1 * | 2/2004 | Boesen ........................ 600/547 |
| 6,731,962 B1 * | 5/2004 | Katarow et al. ............. 600/323 |
| 6,885,191 B1 | 4/2005 | Gleman |
| 6,893,396 B2 | 5/2005 | Schulze et al. |
| 6,909,420 B1 | 6/2005 | Nicolas et al. |
| 7,020,508 B2 | 3/2006 | Stivoric et al. |
| 7,103,578 B2 | 9/2006 | Beck et al. |
| 7,125,382 B2 | 10/2006 | Zhou et al. |
| 7,206,630 B1 * | 4/2007 | Tarler ........................ 600/509 |
| 7,270,633 B1 | 9/2007 | Goscha et al. |
| 7,294,105 B1 | 11/2007 | Islam |
| 7,376,234 B1 | 5/2008 | Gardiner |
| 7,382,247 B2 | 6/2008 | Welch et al. |
| 7,571,369 B2 * | 8/2009 | Wang et al. .................. 714/755 |
| 7,602,301 B1 | 10/2009 | Stirling et al. |
| 7,603,255 B2 | 10/2009 | Case et al. |
| 7,733,224 B2 | 6/2010 | Tran |
| 7,969,307 B2 | 6/2011 | Peeters |
| 8,611,319 B2 | 12/2013 | Magar et al. |
| 2001/0003163 A1 | 6/2001 | Bungert et al. |
| 2001/0047127 A1 | 11/2001 | New et al. |
| 2002/0065828 A1 | 5/2002 | Goodspeed |
| 2003/0004403 A1 | 1/2003 | Drinan et al. |
| 2003/0139903 A1 | 7/2003 | Zweig et al. |
| 2003/0219035 A1 | 11/2003 | Schmidt |
| 2003/0236103 A1 | 12/2003 | Tamaki et al. |
| 2004/0013097 A1 | 1/2004 | Massa |
| 2004/0077975 A1 | 4/2004 | Zimmerman |
| 2004/0199056 A1 | 10/2004 | Husemann et al. |
| 2004/0236192 A1 | 11/2004 | Necola Shehada et al. |
| 2005/0035852 A1 | 2/2005 | Paulsen |
| 2005/0090718 A1 | 4/2005 | Dodds |
| 2005/0101841 A9 | 5/2005 | Kaylor et al. |
| 2005/0113167 A1 | 5/2005 | Buchner et al. |
| 2005/0119533 A1 | 6/2005 | Sparks et al. |
| 2005/0197680 A1 | 9/2005 | Delmain et al. |
| 2005/0206518 A1 | 9/2005 | Welch et al. |
| 2005/0282633 A1 | 12/2005 | Nicolas et al. |
| 2006/0004303 A1 | 1/2006 | Weidenhaupt et al. |
| 2006/0025657 A1 | 2/2006 | Rosenfeld et al. |
| 2006/0031102 A1 | 2/2006 | Teller et al. |
| 2006/0103534 A1 | 5/2006 | Arms et al. |
| 2006/0122473 A1 | 6/2006 | Kill et al. |
| 2006/0122474 A1 | 6/2006 | Teller et al. |
| 2006/0264767 A1 | 11/2006 | Shennib |
| 2007/0027388 A1 * | 2/2007 | Chou ............................ 600/393 |
| 2007/0081505 A1 * | 4/2007 | Roberts ........................ 370/338 |
| 2007/0087780 A1 | 4/2007 | Nassimi |
| 2007/0100219 A1 * | 5/2007 | Sweitzer et al. ............. 600/323 |
| 2007/0135866 A1 | 6/2007 | Baker et al. |
| 2007/0208233 A1 * | 9/2007 | Kovacs ........................ 600/300 |
| 2007/0208262 A1 | 9/2007 | Kovacs |
| 2007/0232234 A1 | 10/2007 | Inzerillo et al. |
| 2007/0244383 A1 | 10/2007 | Talbot et al. |
| 2007/0279217 A1 | 12/2007 | Venkatraman et al. |
| 2007/0282218 A1 | 12/2007 | Yarden |
| 2008/0001735 A1 | 1/2008 | Tran |
| 2008/0054880 A1 | 3/2008 | Miyauchi et al. |
| 2008/0065877 A1 | 3/2008 | Son et al. |
| 2008/0119707 A1 | 5/2008 | Stafford |
| 2008/0139894 A1 * | 6/2008 | Szydlo-Moore et al. ...... 600/300 |
| 2008/0252596 A1 | 10/2008 | Bell et al. |
| 2009/0037670 A1 | 2/2009 | Rofougaran |
| 2009/0051544 A1 | 2/2009 | Niknejad |
| 2009/0316618 A1 | 12/2009 | Fielding et al. |
| 2010/0013607 A1 | 1/2010 | Sabo et al. |
| 2010/0049006 A1 | 2/2010 | Magar et al. |
| 2010/0160746 A1 | 6/2010 | Venkatraman et al. |
| 2010/0316043 A1 | 12/2010 | Doi et al. |
| 2011/0019595 A1 | 1/2011 | Magar et al. |
| 2011/0019824 A1 | 1/2011 | Sattiraju et al. |
| 2012/0256492 A1 * | 10/2012 | Song et al. ..................... 307/66 |
| 2014/0091947 A1 | 4/2014 | Magar et al. |

FOREIGN PATENT DOCUMENTS

| | | |
|---|---|---|
| GB | 2420628 A | 5/2006 |
| JP | 2006055530 A | 3/2006 |
| KR | 10-2004-0032451 | 4/2004 |
| KR | 10-2004-0074056 | 8/2004 |
| KR | 10-2005-0072558 | 7/2005 |
| KR | 10 2005-0116274 | 12/2005 |
| KR | 10-2007-0048168 | 5/2007 |
| WO | WO 89/02682 A1 | 3/1989 |
| WO | WO 89/04093 A1 | 5/1989 |
| WO | WO 89/04578 A1 | 5/1989 |
| WO | WO 98/10617 A1 | 3/1998 |
| WO | WO 02/25773 A1 | 3/2002 |
| WO | WO 02/064032 A2 | 8/2002 |
| WO | WO 02/64032 A3 | 2/2003 |
| WO | WO 03/015005 A2 | 2/2003 |
| WO | WO 03/015838 A2 | 2/2003 |
| WO | WO 03/015005 A3 | 12/2003 |
| WO | WO 2004/002301 A2 | 1/2004 |
| WO | WO 03/015838 A3 | 4/2004 |
| WO | WO 2004/002301 A3 | 4/2004 |
| WO | WO 03/015838 A3 | 5/2004 |
| WO | WO 2004/084720 A2 | 10/2004 |
| WO | WO 2004/084720 A3 | 3/2005 |
| WO | WO 2005/029242 A2 | 3/2005 |
| WO | WO 2005/029242 A3 | 6/2005 |

(56) References Cited

FOREIGN PATENT DOCUMENTS

| WO | WO 2006/094513 A2 | 9/2006 |
|----|-------------------|--------|
| WO | WO 2006/094513 A3 | 4/2007 |
| WO | WO 2008/035151 A2 | 3/2008 |
| WO | WO 2008/097316 A1 | 8/2008 |
| WO | WO 2008/035151 A3 | 12/2008 |

OTHER PUBLICATIONS

Berrou, et al. Near Shannon limit error-correcting coding and decoding: Turbo-codes. 1. IEEE Int. Conf. Commun., vol. 2, Geneva, Switzerland, May 1993, p. 1064-1070.
International Search Report dated Nov. 19, 2007 for PCT application No. 2007/062772.
Vucetic, et al. Turbo Codes: Principles and Applications. The Kluwer International Series in Engineering and Computer Science). Kluwer Academic Publishers, 2000. (Table of Contents pages only) (8 pages).
International Search Report and written opinion dated Mar. 19, 2009 for PCT application No. 2008/073739.
International search report and written opinion dated Nov. 19, 2007 for PCT application No. 2007/062772.
International search report and written opinion dated Jan. 22, 2009 for PCT application No. 2008/080716.
International search report and written opinion dated Feb. 24, 2009 for PCT application No. 2008/073591.
International search report and written opinion dated Apr. 24, 2009 for PCT application No. 2008/081010.
UK combined search and examination report dated Sep. 12, 2011 for Application No. GB0815326.4.
Office action dated Apr. 4, 2013 for U.S. Appl. No. 12/702,127.
UK combined search and examination report dated Jun. 26, 2012 for Application No. GB 1210339.6.
UK combined search and examination report dated Jun. 27, 2012 for Application No. GB 1210351.1.
Office action dated Aug. 13, 2013 for U.S. Appl. No. 12/193,865.
European search report dated Apr. 5, 2012 for EP Application No. 08841472.7.
Office action dated Feb. 13, 2013 for U.S. Appl. No. 12/739,519.
Office action dated Feb. 24, 2011 for U.S. Appl. No. 12/193,865.
Office action dated Mar. 29, 2012 for U.S. Appl. No. 12/739,549.
Office action dated Apr. 3, 2012 for U.S. Appl. No. 12/739,519.
Office action dated Jun. 21, 2012 for U.S. Appl. No. 12/193,865.
Office action dated Aug. 7, 2009 for U.S. Appl. No. 11/756,161.
Office action dated Oct. 5, 2012 for U.S. Appl. No. 12/739,549.
Office action dated Nov. 28, 2011 for U.S. Appl. No. 12/193,865.
Office action dated Jul. 9, 2013 for U.S. Appl. No. 12/096,195.
U.S. Appl. No. 14/099,842, filed Dec. 6, 2013, Magar et al.
European search report and search opinion dated Apr. 16, 2014 for EP Application No. 07757453.1.
Office action dated May 22, 2014 for U.S. Appl. No. 12/702,127.
Office action dated Jun. 19, 2014 for U.S. Appl. No. 12/096,195.
Office action dated Jul. 8, 2014 for U.S. Appl. No. 12/739,549.
Office action dated Apr. 25, 2014 for U.S. Appl. No. 12/193,865.

\* cited by examiner

WIRELESS PHYSIOLOGICAL SENSOR PATCHES AND SYSTEMS

CROSS-REFERENCE

This application claims the benefit of U.S. Provisional Application No. 60/968,023, filed Aug. 24, 2007, which application is incorporated herein by reference in its entirety.

BACKGROUND OF THE INVENTION

Monitoring the health of people has always been important. As the population ages and more people advance in age, health monitoring systems become more significant to maintaining a healthy lifestyle and disease management. Remote health monitoring makes it easier and cost effective to monitor the health of vast populations. Wireless systems are the most desired approach to enable remote health monitoring. Therefore, a variety of wireless health monitoring systems have been introduced over the years.

Conventional wireless health monitoring systems are bulky, expensive, have inadequate wireless link reliability and have high power dissipation which severely limits their applications, particularly to monitor wide ranging physiological parameters in high volumes for large populations. Accordingly, what is desired is a system that addresses the above-identified issues.

SUMMARY OF THE INVENTION

One aspect of the invention is an asymmetric system comprising: two or more ASIC chips wherein the chips are designed to work together to measure physiological signals, comprising: (a) a patch-ASIC chip adapted for incorporation into a physiological signal monitoring patch comprising a sensor interface, a processor coupled to the sensor interface, a memory element coupled to the processor, a radio coupled to the memory element that transmits data to a base-ASIC chip, and power management circuits that coordinate power usage on the chip; and (b) the base-ASIC chip, comprising a processor that processes sensor data, a memory element coupled to the processor, a radio coupled to the memory element that communicates instructions to the patch-ASIC chip, power management circuits for coordinating power usage on the chip, and a host interface through which the base-ASIC chip communicates with a host device;

In some embodiments the base-ASIC chip has more processing resources than the patch-ASIC chip.

In some embodiments the base-ASIC has a higher silicon area than the patch-ASIC chip. In some embodiments the ratio of silicon area of the base-ASIC chip to the patch-ASIC chip is at least about 2:1. In some embodiments the ratio of silicon area of the base-ASIC chip to the patch-ASIC chip is at least about 4:1.

In some embodiments the patch-ASIC chip comprises low-complexity transmitters and low complexity receivers, and the base-ASIC chip comprises high-complexity transmitters and high complexity receivers.

In some embodiments the patch-ASIC chip comprises a UWB transmitter and a narrowband receiver, and the base-ASIC chip comprises a narrow band transmitter and a UWB receiver.

In some embodiments the patch-ASIC chip comprises a turbo encoder, and the base-ASIC chip comprises a turbo-decoder. In some embodiments the patch-ASIC chip communicates through a single antenna, and the base-ASIC chip communicates through multiple antennas. In some embodiments the base-ASIC chip further comprises smart antenna processing. In some embodiments the base-ASIC chip, comprises processors for analyzing the radio environment. In some embodiments the system comprises a base-ASIC chip and multiple patch-ASIC chips.

One aspect of the invention is a method comprising: monitoring a physiological condition using two or more ASIC chips and a host device wherein the chips are designed to work together to measure physiological signals comprising: (a) receiving signals from a sensor at a patch-ASIC chip that is incorporated into a physiological signal monitoring patch, the patch-ASIC chip comprising a sensor interface coupled to the sensor, a processor coupled to the sensor interface, a memory element coupled to the processor, a radio coupled to the memory element; (b) transmitting data signals from the radio on the patch-ASIC chip through an antenna incorporated into the patch; (c) receiving the data signals at a base-ASIC chip comprising an antenna that sends the signals to a processor that processes data signals, a memory element coupled to the processor, a radio coupled to the memory element, and a host interface through which the base-ASIC chip communicates with a host device; and (d) transmitting instructions wirelessly from the base-ASIC chip to the patch-ASIC chip; wherein the base-ASIC chip consumes more power than the patch-ASIC chip.

In some embodiments the ratio of power consumed by the base-ASIC chip to the power consumed by the patch-ASIC chip measured during continual data transmission is 2:1. In some embodiments the ratio of power consumed by the base-ASIC chip to the power consumed by the patch-ASIC chip measured during continual data transmission is 4:1.

One aspect of the invention is a system comprising two or more ASIC chips wherein the chips are designed to work together to measure physiological signals, comprising: (a) a patch-ASIC chip adapted for incorporation into a physiological signal monitoring patch comprising a sensor interface, a processor coupled to the sensor interface, a memory element coupled to the processor, a radio coupled to the memory element that transmits data to a base-ASIC chip, and power management circuits that coordinate power on the chip; and (b) the base-ASIC chip comprising a processor that processes sensor data, a memory element coupled to the processor, a radio coupled to the memory element that that transmits instructions to the patch-ASIC chip, power management circuits for coordinating power on the chip, and a host interface through which the base-ASIC chip communicates with a host device.

In some embodiments the base-ASIC chip is incorporated into a μ-Base and the patch-ASIC chip is incorporated into a μ-Patch, wherein each of the μ-Base and the μ-Patch comprise a printed circuit board and an antenna attached to the printed circuit board for transmitting radio signals. In some embodiments the base-ASIC chip acts as a master device to coordinate a function of the μ-Patch. In some embodiments a function coordinated by the base-ASIC chip is initialization and link set up, power management, data packet routing, type of transmission radio, radio transmit-power, radio receive-sensitivity, patch operational integrity, audio tone generation, display activation, or a combination thereof. In some embodiments the base-ASIC chip can coordinate the bias of the RF circuitry on the patch-ASIC chip to coordinate energy usage on the patch.

In some embodiments the base-ASIC chip is incorporated into the host device; wherein the host device comprises a stationary, portable, or mobile device or a stationary, portable, or mobile medical instrument. In some embodiments the base-ASIC chip is incorporated into an adapter which plugs into the host device; wherein the host device comprises a stationary, portable or mobile device or a stationary, portable, or mobile medical instrument. In some embodiments the adapter comprising the base-ASIC chip plugs into a medical instrument through a serial interface connection. In some embodiments the adapter provides physiological information from wireless sensors to a stationary, portable, or mobile medical instrument that was designed for receiving physiological information from wired sensors, wherein the adapter allows the medical instrument to receive substantially equivalent information from the wireless sensors. In some embodiments the adapter allows a medical instrument which is designed to be connected to sensors by wires to be compatible with sensors that transmit wirelessly. In some embodiments the base-ASIC chip is incorporated into a cell phone.

In some embodiments the patch-ASIC chip and the base-ASIC chip are each part of an ASIC superset chip, wherein the functionality of both the patch-ASIC chip and the base-ASIC chip are contained on the ASIC superset chip, and wherein un-used portions of the superset chip are turned off on the patch-ASIC chip or the base-ASIC chip.

In some embodiments the two or more ASIC chips can send and/or receive both ultrawide band (UWB) radio and narrowband radio signals. In some embodiments the base-ASIC chip can switch the transmission mode of the patch-ASIC chip between UWB and narrowband radio. In some embodiments the patch-ASIC chip comprises an encoding scheme for encoding data transmission and the base-ASIC chip comprises a decoding scheme for decoding data transmission from the µ-Patch. In some embodiments the system provides security by an encryption scheme using shared keys, wherein the device comprising the base-ASIC chip wirelessly exchanges the shared keys with the patch. In some embodiments the ASIC chips can avoid or minimize interference by pseudo-random hopping of carrier frequencies, or by data modulation with pseudo-random code sequences. In some embodiments the system provides reliability by forward-error correction, packet-retransmission by automatic repeat request (ARQ), and/or smart antenna techniques.

In some embodiments the µ-Patch comprises one antenna and the µ-Base comprises 2 or more antennas. In some embodiments the µ-Patch performs compression of the radio signal and the µ-Base performs decompression of the radio signal.

In some embodiments the µ-Base further comprise a power amplifier external to the base-ASIC chip for amplifying sensor data signal. In some embodiments the µ-Base can transmit at 5 times higher power than the µ-Patch.

In some embodiments the system comprises one base-ASIC chip and multiple patch-ASIC chips.

In some embodiments the µ-Patch uses on average less than about 6 mW of power. In some embodiments the patch-ASIC chip can transmit more than about 1 KB of data per day to the base-ASIC chip. In some embodiments the patch-ASIC chip can transmit more than about 1 KB of data per day at a range of up to 30 m to the base-ASIC chip.

One aspect of the invention is a system comprising three or more ASIC chips wherein the chips are designed to work together to measure physiological signals, comprising: (a) a patch-ASIC chip adapted for incorporation into a physiological signal monitoring patch comprising a sensor interface, a processor coupled to the sensor interface, a memory element coupled to the processor, a radio coupled to the memory element that transmits sensor data to a base-ASIC chip and/or a gate-ASIC chip, and power management circuits that coordinate power on the chip; (b) the gate-ASIC chip comprising a processor that processes sensor data, a memory element coupled to the processor, a radio coupled to the processor that communicates with the patch-ASIC chip and the base-ASIC chip, and power management circuits that coordinate power on the chip; and (c) the base-ASIC chip comprising a processor that processes sensor data, a memory element coupled to the processor, a radio coupled to the memory element that that transmits instructions to the patch-ASIC chip and/or the gate-ASIC chip, power management circuits that coordinate power on the chip, and a host interface through which the base-ASIC chip communicates with a host device.

In some embodiments the base-ASIC chip is incorporated into a µ-Base, the patch-ASIC chip is incorporated into a µ-Patch, and the gate-ASIC chip is incorporated into a µ-Gate; wherein each of the µ-Base, µ-Patch, and µ-Gate comprise a printed circuit board and an antenna attached to the printed circuit board for transmitting radio signals.

In some embodiments the gate-ASIC chip further comprises a sensor interface for receiving signals from sensors, wherein the µ-Gate is incorporated into a patch. In some embodiments the µ-Patch only transmits UWB, and the µ-Gate has both a UWB and a narrowband radio. In some embodiments the base-ASIC chip acts as a master device to coordinate a function of the µ-Patch or the µ-Gate or both the µ-Patch and the µ-Gate. In some embodiments the base-ASIC chip can switch the transmission mode of the µ-Patch and/or the µ-Gate between UWB and narrowband radio.

In some embodiments the base-ASIC chip is incorporated into the host device; wherein the host device comprises a stationary, portable, or mobile device or a stationary, portable, or mobile medical instrument. In some embodiments the base-ASIC chip is incorporated into an adapter which plugs into the host device; wherein the host device comprises a stationary, portable or mobile device or a stationary, portable, or mobile medical instrument.

In some embodiments the gate-ASIC chip communicates wirelessly with both the patch-ASIC chip and the base-ASIC chip.

In some embodiments the patch-ASIC chip and the gate-ASIC chip are each members of an ASIC superset; and wherein the unused portions on the patch-ASIC chip and/or the base-ASIC are turned off. In some embodiments the patch-ASIC chip, the gate-ASIC chip and the base-ASIC chip are each part of an ASIC superset chip, wherein the functionality of two or more of the patch-ASIC chip, the gate-ASIC chip and the base-ASIC chip are contained on the ASIC superset chip, and wherein un-used portions of the superset chip are turned off on the patch-ASIC chip, the gate-ASIC chip, or the base-ASIC chip. In some embodiments the adapter comprising the base-ASIC chip plugs into a medical instrument through a serial interface connection. In some embodiments adapter provides physiological information from wireless sensors to a stationary, portable, or mobile medical instrument that was designed for receiving physiological information from wired sensors, wherein the adapter allows the medical instrument to receive substantially equivalent information from the wireless sensors. In some embodiments the adapter allows a medical instrument which is designed to be connected to sensors by wires to be compatible with sensors that transmit wirelessly.

One aspect of the invention is a patch for measuring a physiological state comprising a battery and an antenna each coupled to an integrated circuit comprising a sensor interface that receives physiological signals from a sensor, a processor coupled to the sensor interface, a memory element coupled to the processor, a radio coupled to the memory element, and power management circuits that coordinate power dissipation on the chip; wherein the area of the patch multiplied by the thickness of the patch is less than about 30 cm$^3$; and wherein the patch can wirelessly transmit physiological data for at least about 2 days while monitoring a physiological signal from the patient without changing or recharging the battery.

In some embodiments the monitoring of the physiological signal is sampled substantially continuously. In some embodiments the signal is sampled substantially continuously at greater than 200 Hz. In some embodiments the patch can wirelessly transmit physiological data for at least about 4 days. In some embodiments the battery provides a charge of about 250 mA-hours or less.

In some embodiments the patch buffers data obtained from monitoring a physiological signal then transmits the data in bursts. In some embodiments the patch uses on average less than about 10 mW of power.

In some embodiments the patch can transmit more than about 1 KB of sensor data per day at a range of up to 30 m. In some embodiments the power management circuits coordinate duty cycle with clock-gating with protocol-level sleep modes. In some embodiments the patch can measure signals in continuous, episodic, and/or periodic modes.

In some embodiments the patch also comprises a sensor. In some embodiments the sensor comprises electrodes and senses electrical signals. In some embodiments the sensor measures EEG, EMG, or ECG signals or combinations thereof.

In some embodiments the ASIC chip can send and/or receive both ultra-wideband (UWB) and narrowband radio signals.

In some embodiments the patch comprises disposable and reusable parts. In some embodiments a sensor and/or the battery are disposable, and substantially all of the electronics are reusable. In some embodiments the patch is disposable.

In some embodiments the sensor is separate from the patch and electrically connected to the patch.

In some embodiments the sensor measures ECG, EEG, EMG, SpO2, tissue impedance, heart rate, accelerometer, blood glucose, PT-INR, respiration rate and airflow volume, body tissue state, bone state, pressure, physical movement, body fluid density, patient physical location, or audible body sounds, or a combination thereof. In some embodiments the patch can generate stimulus signals that are detected by sensors connected to or incorporated into the patch or connected to or incorporated into another patch. In some embodiments the stimulus signals are electrical, ultrasound, or radio wave signals. In some embodiments the electrical signals are used to measure skin or body impedance.

In some embodiments the patch comprises an alert which is an audio signal generator or a visual display. In some embodiments the battery can be re-charged via electromagnetic induction.

One aspect of the invention is a patch for measuring a physiological state comprising a battery and an antenna each coupled to an integrated circuit comprising a sensor interface that receives physiological signals from a sensor, a processor coupled to the sensor interface, a memory element coupled to the processor, a radio coupled to the memory element, and power management circuits that coordinate power dissipation on the chip; wherein the patch is a cardiac patch that can measure all of ECG, SpO2, tissue impedance, accelerometer, and PT-INR signals.

One aspect of the invention is a patch for measuring a physiological state comprising a battery and an antenna each coupled to an integrated circuit comprising a sensor interface that receives physiological signals from a sensor, a processor coupled to the sensor interface, a memory element coupled to the processor, a radio coupled to the memory element, and power management circuits that coordinate power dissipation on the chip; wherein the patch is a neurological patch for measuring sleep apnea that can measure all of EEG, EMG, SpO2, heart rate, respiration rate and airflow volume, and pressure signals.

One aspect of the invention is a patch for measuring a physiological state comprising a battery and an antenna each coupled to an integrated circuit comprising a sensor interface that receives physiological signals from a sensor, a processor coupled to the sensor interface, a memory element coupled to the processor, a radio coupled to the memory element, and power management circuits that coordinate power dissipation on the chip; wherein the patch is an endocrinological patch for measuring diabetes or wounds that can measure all of ECG, blood glucose, and UWB radar signals.

One aspect of the invention is a patch for measuring a physiological state comprising a battery and an antenna each coupled to an integrated circuit comprising a sensor interface that receives physiological signals from a sensor, a processor coupled to the sensor interface, a memory element coupled to the processor, a radio coupled to the memory element, and power management circuits that coordinate power dissipation on the chip; wherein the patch is fitness and wellness patch that can measure all of ECG, heart rate, accelerometer, and pressure signals.

One aspect of the invention is a method comprising monitoring a physiological condition using two or more ASIC chips and a host device wherein the chips are designed to work together to measure physiological signals comprising: (a) receiving signals from a sensor at a patch-ASIC chip that is incorporated into a physiological signal monitoring patch, the patch-ASIC chip comprising a sensor interface coupled to the sensor, a processor coupled to the sensor interface, a memory element coupled to the processor, a radio coupled to the memory element; (b) managing the power dissipation on the patch-ASIC chip with power management circuits on the patch-ASIC chip; (c) transmitting data signals from the radio on the patch-ASIC chip through an antenna incorporated into the patch; (d) receiving the data signals at a base-ASIC chip comprising a processor that processes data signals, a memory element coupled to the processor, a radio coupled to the memory element, power management circuits that coordinate power dissipation on the base-ASIC chip, and a host interface through which the base-ASIC chip communicates with a host device; and (e) sending instructions wirelessly from the base-ASIC chip to the patch-ASIC chip such that the base-ASIC chip coordinates a function of the physiological signal monitoring patch.

In some embodiments a function coordinated by the base-ASIC chip is initialization and link set up, power management, data packet routing, type of transmission radio, radio transmit-power, radio receive-sensitivity, patch operational integrity, audio signal generation, display activation, or a combination thereof. In some embodiments the ASIC chips function on a packet-data protocol and the base-ASIC chip coordinates data packet routing. In some embodiments the base-ASIC chip keeps track of the quality of the wireless links between ASIC chips and sends commands to the patch-ASIC chip and/or gate-ASIC chips to instruct the chips to switch between UWB and narrowband radio or to raise or lower transmit power in order to lower power consumption or to enhance communication quality. In some embodiments the patch-ASIC chip is authenticated by bringing the physiological monitoring patch in proximity of the device comprising the base-ASIC chip.

In some embodiments the authentication is provided by an encryption scheme using shared keys, wherein the device comprising the base-ASIC chip wirelessly exchanges the shared keys with the patch. In some embodiments the encryption scheme is an Advanced Encryption Standard (AES) scheme. In some embodiments a user is alerted with an audio and/or a visual signal. In some embodiments the audio and/or visual signal is generated on the patch. In some embodiments the audio and/or visual signal is generated on a device to which the base-ASIC chip is connected.

In some embodiments the method is used to manage a patient disease. In some embodiments the patient disease is arrhythmia, heart failure, coronary heart disease, diabetes, sleep apnea, seizures, asthma, COPD, pregnancy complications, and wound state or combinations thereof. In some embodiments the method is used to manage a condition related to the state of wellness and fitness of a person. In some embodiments the condition being managed is weight loss, obesity, heart rate, cardiac performance, dehydration rate, blood glucose, physical activity or caloric intake, or combinations thereof.

A method comprising monitoring a physiological condition using three or more ASIC chips wherein the chips are designed to work together to measure physiological signals, comprising: (a) receiving physiological signals from sensors at a patch-ASIC chip incorporated into a physiological signal monitoring patch, the patch-ASIC chip comprising a sensor interface, a processor coupled to the sensor interface, a memory element coupled to the processor, a radio coupled to the memory element; (b) managing power dissipation on the patch-ASIC chip with power management circuits on the patch-ASIC chip; (c) transmitting data to a base-ASIC and/or a gate-ASIC chip through an antenna in the patch; (d) receiving the data sent from the patch-ASIC chip at the gate-ASIC chip, the gate-ASIC chip comprising a processor that processes sensor data, a memory element coupled to the processor, a radio coupled to the processor that communicates with the patch-ASIC chip and the base-ASIC chip, and power management circuits for coordinating power dissipation on the gate-ASIC chip; (e) coordinating a function on the patch-ASIC chip and/or gate-ASIC chip by sending instructions from a base-ASIC chip to the patch-ASIC chip and/or the gate-ASIC chip, wherein the base-ASIC chip comprises a processor that processes sensor data, a memory element coupled to the processor, a radio coupled to the memory element, power management circuits for coordinating power dissipation on the base-ASIC chip; and (f) sending data from the base-ASIC chip to a host device through a host interface.

In some embodiments the base-ASIC chip is incorporated into a μ-Base, the patch-ASIC chip is incorporated into a μ-Patch, and the gate-ASIC chip is incorporated into a μ-Gate; wherein each of the μ-Base, μ-Patch, and μ-Gate comprise a printed circuit board and an antenna attached to the printed circuit board for transmitting and receiving radio signals.

In some embodiments the gate-ASIC chip further comprises a sensor interface for receiving signals from sensors, wherein the gate-ASIC is incorporated into a patch.

In some embodiments the μ-Patch only transmits UWB, and the μ-Gate comprises both UWB and narrowband radios.

In some embodiments the base-ASIC chip acts as a master device to coordinate a function of the μ-Patch or the μ-Gate or both the μ-Patch and the μ-Gate. In some embodiments the base-ASIC chip keeps track of the quality of the wireless links between ASIC chips and sends commands to the patch-ASIC chip and/or gate-ASIC chips to instruct the chips to switch between UWB and narrowband radio or to raise or lower transmit power in order to lower power consumption or to enhance communication quality. In some embodiments the base-ASIC chip is incorporated into the host device; wherein the host device comprises a stationary, portable, or mobile device or a stationary, portable, or mobile medical instrument.

In some embodiments the base-ASIC chip is incorporated into an adapter which plugs into the host device; wherein the host device comprises a stationary, portable or mobile device or a stationary, portable, or mobile medical instrument. In some embodiments the gate-ASIC chip communicates wirelessly with both the patch-ASIC chip and the base-ASIC chip. In some embodiments the patch-ASIC chip and the gate-ASIC chip are each members of an ASIC superset; and wherein an unused function on the patch-ASIC chip is turned off.

In some embodiments the patch-ASIC chip, the gate-ASIC chip and the base-ASIC chip are each part of an ASIC superset chip, wherein the functionality of two or more of the patch-ASIC chip, the gate-ASIC chip and the base-ASIC chip are contained on the ASIC superset chip, and wherein un-used portions of the superset chip are turned off on the patch-ASIC chip, the gate-ASIC chip, or the base-ASIC chip.

In some embodiments the base-ASIC chip is incorporated into an adapter which plugs into the host device; wherein the host device comprises a stationary, portable or mobile device or a stationary, portable, or mobile medical instrument. In some embodiments the adapter comprising the base-ASIC chip plugs into a medical instrument through a serial interface connection. In some embodiments the adapter provides physiological information from wireless sensors to a stationary, portable, or mobile medical instrument that was designed for receiving physiological information from wired sensors, wherein the adapter allows the medical instrument to receive substantially equivalent information from the wireless sensors. In some embodiments the adapter allows a medical instrument which is designed to be connected to sensors by wires to be compatible with sensors that transmit wirelessly.

One aspect of the invention is a method comprising receiving physiological signals from sensors at a patch wherein the patch comprises a battery and an antenna each coupled to an integrated circuit comprising a sensor interface that receives the physiological signals from the sensor, a processor coupled to the sensor interface that receives signals from the sensor interface and processes the signals, a memory element coupled to the processor that receives and stores signals, and a radio coupled to the memory element that sends signals received from the memory element to an antenna, wherein power management circuits coordinate power dissipation on the chip; wherein the area of the patch multiplied by the thickness of the patch is less than about 30 cm$^3$; and wherein the patch can wirelessly transmit physiological data for at least about 2 days while monitoring a physiological signal from the patient without changing or recharging the battery. In some embodiments the monitoring of the physiological signal is sampled substantially continuously. In some embodiments the signal is sampled substantially continuously at greater than 200 Hz. In some embodiments method can wirelessly transmit physiological data for at least about 4 days. In some embodiments the battery provides a charge of about 250 mA-hours or less. In some embodiments the patch buffers data obtained from monitoring a physiological signal then transmits the data in bursts. In some embodiments the patch uses on average less than about 10 mW of power. In some embodiments the patch can transmit more than about 1 KB of sensor data per day at a range of up to 30 m. In some embodiments the power management circuits coordinate duty cycle with clock-gating with protocol-level sleep modes.

In some embodiments the patch can measure signals in continuous, episodic, and/or periodic modes.

In some embodiments the patch also comprises the sensor. In some embodiments the sensor comprises electrodes and senses electrical signals. In some embodiments the sensor measures EEG, EMG and ECG signals or combinations thereof. In some embodiments the ASIC chip can send and/or receive both ultra-wideband (UWB) and narrowband radio signals.

In some embodiments the patch comprises disposable and reusable parts. In some embodiments a sensor and/or the battery are disposable, and substantially all of the electronics are reusable. In some embodiments the patch is disposable.

In some embodiments the sensor is separate from the patch and electrically connected to the patch. In some embodiments the sensor measures ECG, EEG, EMG, SpO2, tissue impedance, heart rate, accelerometer, blood glucose, PT-INR, respiration rate and airflow volume, body state, bone state, pressure, physical movement, body fluid density, patient physical location, or audible body sounds, or a combination thereof. In some embodiments the method can generate stimulus signals that are detected by sensors connected to or incorporated into the patch or connected to or incorporated into another patch. In some embodiments the stimulus signals are electrical, ultrasound, or radio wave signals. In some embodiments the electrical signals are used to measure skin or body impedance. In some embodiments the patch comprises an alert which is an audio signal generator or a visual display. In some embodiments the battery can be re-charged magnetically.

In some embodiments the patch is a cardiac patch that can measure all of ECG, SpO2, tissue impedance, accelerometer, and PT-INR signals. In some embodiments the patch is a neurological patch for measuring sleep apnea that can measure all of EEG, EMG, SpO2, heart rate, respiration rate and airflow volume, and pressure signals. In some embodiments the patch is an endocrinological patch for measuring diabetes or wounds that can measure all of ECG, blood glucose, and UWB radar signals. In some embodiments the patch is fitness and wellness patch that can measure all of ECG, heart rate, accelerometer, and pressure signals.

One aspect of the invention is a method for unsupervised placement of a physiological patch comprising: (a) placing the patch that can receive wireless signals from a base device, wherein the patch comprises a visual marker to help the user orient the patch on the patient's body; (b) initializing the patch with a base device by automatic verification of proper placement of the patch; and (c) indicating the proper or improper placement of the patch to the user with an audio or visual indication.

One aspect of the invention is a business method comprising: a) manufacturing both a patch-ASIC chip and a base-ASIC chip designed to work together to wirelessly communicate physiological data, wherein each chip each comprises a processor, memory storage, a wireless radio, and circuits for power management, wherein the chips are designed to be used with a plurality sensor types; and (b) selling and/or licensing the patch-ASIC chip and base-ASIC chip to multiple customers for incorporation into physiological sensing systems.

In some embodiments, the plurality of sensor types include sensors that measure all of ECG, EEG, EMG, SpO2, tissue impedance, heart rate, and accelerometer signals.

The business method may further comprise a gate-ASIC chip designed to work together with the patch-ASIC chip and the base-ASIC chip, to wirelessly communicate physiological data, wherein each chip each comprises a processor, memory storage, a wireless radio, and circuits for power management, wherein the chips are designed to be used with a plurality sensor types.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
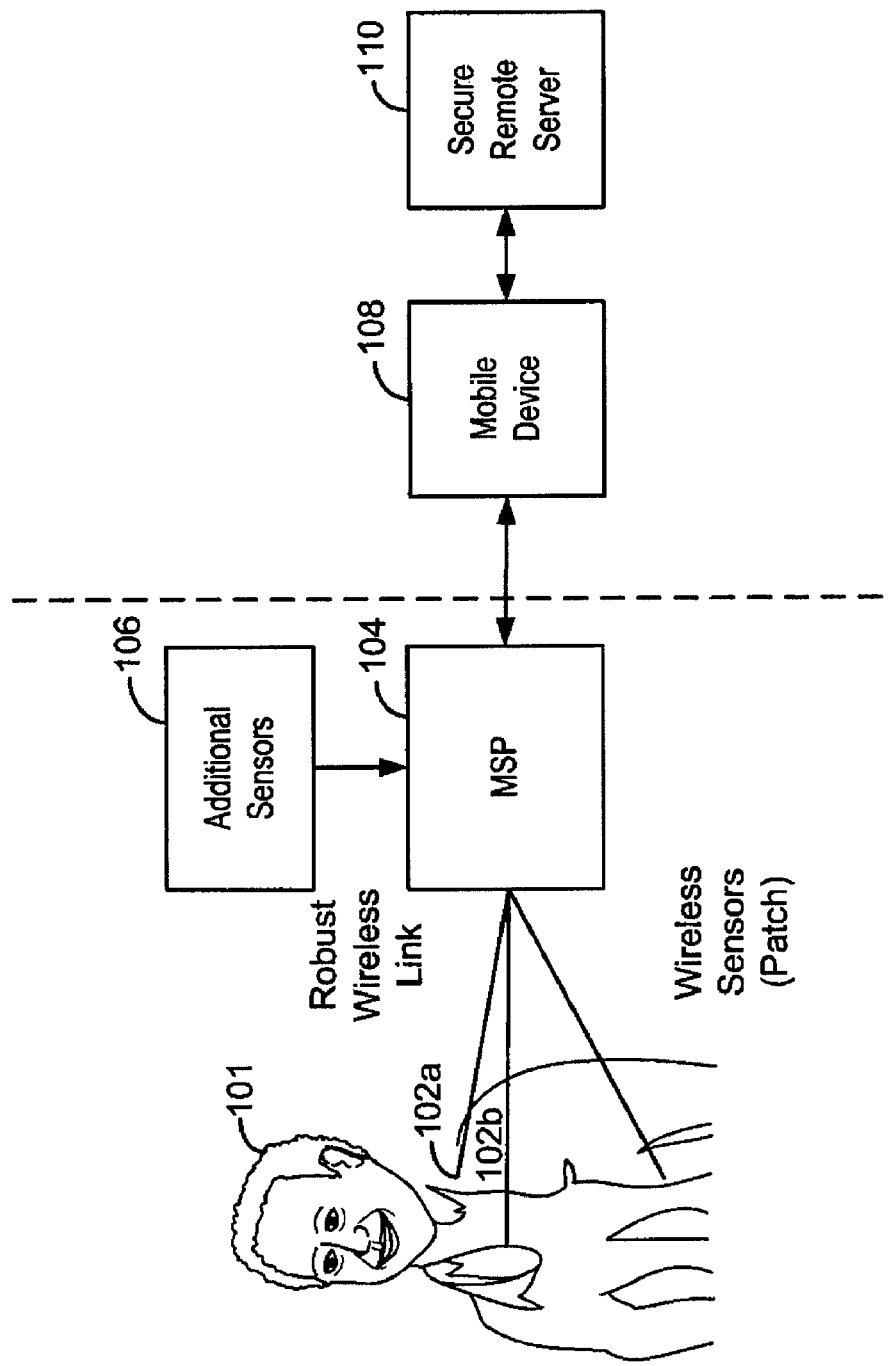
FIG. 1A is a block diagram of a first embodiment of a general architecture of wireless health monitoring system in accordance with the present invention.

The current invention relates to patches, integrated circuits (chips), systems and methods for a wireless medical signal processing system for health monitoring which can achieve high wireless link reliability/security, low power dissipation, compactness, low cost and supports a variety of sensors for various physiological parameters. One aspect of the invention is a wireless system for monitoring physiological conditions comprising two or more ASIC chips that are designed to work together to optimize the performance of a wireless monitoring system. One of the ASIC chips is designed to be incorporated into a patch attached to a patient (the patch-ASIC chip), and one of the ASIC chips is incorporated into a mobile or stationary device (the base-ASIC chip). Typically, the base-ASIC chip will be incorporated into a device that will tend to be in the vicinity of the patient. The two or more ASIC chips are designed in order to improve the performance of the system by distributing the different aspects of functionality between the different chip types. Thus the ASIC chips are designed to function in an asymmetric manner in which the base-ASIC will perform more of the processing intensive tasks. In some cases, the base-ASIC will perform all or a majority of functions of a particular type, while the patch-ASIC chip may perform all or a majority of functions of another type. This asymmetric design of the sets of ASIC chips can improve the performance of the physiological monitoring system resulting in better management of power, lower cost, and higher reliability.

In one aspect, the base-ASIC chip is designed to coordinate some of the functions on the patch through the patch-ASIC chip. In many cases, the base-ASIC is incorporated such that it has access to much more power and energy than does the patch-ASIC chip. Thus, the system of the current invention comprises an asymmetric system in which the base-ASIC chip takes on more power and processor intensive functions. This approach can result in lower power dissipation at the patch, which can in turn result in a physiological monitoring system in which the patch can collect and transmit data for days or weeks without recharging or replacing batteries. In addition, the base-ASIC can control the flow of data in a network of patches in order to improve the management of data relating to signals, increasing the amount and quality of physiological information. For example, the base-ASIC chip can supervise and control the functions of the patch-ASIC chip, for example by controlling duty cycle, transmission mode, transmission rate, and transmission timing. The base-ASIC and patch-ASIC chips can be designed such that the coding/decoding functions are asymmetric. For example, the patch-ASIC can be build to carry out Turbo encoding, which is relatively simple, and the base-ASIC can be designed to carry out Turbo-decoding which is more complex, and requires more processing power and therefore uses more energy. Another aspect of asymmetric design of the ASIC chips involves providing a complex antenna scheme such as the use of multiple antennas with smart antenna processing on the base-ASIC, and the use of a single antenna with simple processing on the gate-ASIC. Another aspect of the asymmetric design is the use of different radio scheme capability on the gate-ASIC and base-ASIC chips. For example, low-complexity transmitters (e.g. UWB) and low-complexity receivers (e.g. Narrow-band) are employed on the on patch-ASIC; and high-complexity transmitters (e.g. Narrow band) and high-complexity receivers (e.g. UWB) are employed on the base-ASIC. Another aspect of the asymmetry has to do with distributing the functions of analyzing and controlling the radio channel. Here, the base-ASIC has all the processors for analyzing the radio environment and sending instructions to patch-ASIC to use a particular radio scheme; and the patch-ASIC has simple circuits to just follow the instructions coming from Base ASIC.

In some embodiments two or more of these distributed aspects are coupled together, for example, where the base-ASIC and patch-ASIC are designed to work together such that the base-ASIC has processors for turbo-decoding, multiple antennas and smart antenna processing capability, and high-complexity transmitters (e.g. Narrow band) and high-complexity receivers (e.g. UWB); and the patch-ASIC has processors for Turbo decoding, the capability of receiving signals from a single antenna, and has low-complexity transmitters (e.g. UWB) and low-complexity receivers.

One aspect of the asymmetric distributed processing of the present invention is a patch-ASIC chip and a base-ASIC chip designed to work together in which the area of the base-ASIC chip is higher than that of the patch-ASIC chip. This difference in area results, for example, from the fact that the base-ASIC chip takes on the more processor intensive operations in carrying out the monitoring of a patient's physical condition. In some embodiments, the area of the base-ASIC chip is more than 2 times the area of the patch-ASIC chip. In some embodiments, the area of the base-ASIC chip is more than 4 times the area of the patch-ASIC chip.

One aspect of the asymmetric distributed processing of the present invention is a method wherein a patch-ASIC chip and a base-ASIC chip designed to work together and in which the power consumed by the base-ASIC chip is higher than the power consumed by the patch-ASIC chip. In some embodiments the power consumed by the base-ASIC is 2 or more times the power consumed by the patch-ASIC chip. In some embodiments the power consumed by the base-ASIC is 4 or more times the power consumed by the patch-ASIC chip. The power consumption (power dissipation) of the chips can be measured, for example during continual data transmission.

In some embodiments of the system the base-ASIC is incorporated into a µ-Base (or medical signal processor (MSP)) comprising a printed circuit board and an antenna attached to the printed circuit board. In some embodiments of the system the patch-ASIC is incorporated into a µ-Patch comprising a printed circuit board and an antenna attached to the printed circuit board. In some embodiments, the antenna is a PCB antenna.

One aspect of the invention is an asymmetric system for wireless monitoring wherein the two ASIC chips are designed such that the base-ASIC chip carries out the more power and processor intensive functions of the system. For example, in some embodiments, the base-ASIC chip carries out smart antenna schemes, which can be processor and power intensive, which allows the µ-Base reliably detect weaker signals, thus allowing the µ-Patch to transmit at lower power, saving energy on the patch. Analogously, in some embodiments, the µ-Base will have multiple antennas, e.g. 4 antennas, for implementation of the smart antenna schemes. In some embodiments, in order to provide reliability for the system while using low power at the patch, the base-ASIC chip carries out decoding functions which are processor and power intensive, while the patch-ASIC chip carries out encoding which is less processor and power intensive. This asymmetric scheme is facilitated in part because of the data transfer asymmetry of the system in many embodiments, in which the patch is transmitting much more data to the µ-Base than the µ-Base is transmitting to the patch because the patch is generally transferring physiological sensor data to the µ-Base, and the µ-Base is sending back mainly instructions to control functions on the patch-ASIC chip and the patch.

The base-ASIC chip can be connected to or built into a stationary, portable, or mobile device. In some embodiments, the base-ASIC chip is connected to or built into a cellular phone, pager, i-Pod™, PDA, or other mobile device that would tend to be carried by or be near the patient. In some embodiments, the base-ASIC chip is connected to or built into a laptop, notebook, palm-top, or desk-top computer. In some embodiments, the base-ASIC chip is connected to or built into a medical instrument for monitoring physiological signals related to health conditions such as ECG, EEG, EMG, $SpO_2$, tissue impedance, heart rate, accelerometer, blood glucose, PT-INR, respiration rate and airflow volume, UWB radar, pressure, physical movement, body fluid density, patient physical location, or audible body sounds. The medical instrument can be stationary, desk-top, portable, or mobile.

In some embodiments, the base-ASIC chip is incorporated into an adaptor that is connected to a medical instrument such as a medical monitor, wherein the adaptor communicates wirelessly with one or more patches having a patch-ASIC chip. The adaptor receives the physiological signal from one or more patches, translates the physiological signal to a signal that is compatible with the medical monitor, and sends the translated signal to the medical monitor. In some embodiments, the adaptor is connected to the medical monitor with the same connector to which the medical monitor connects to wired sensors. In some embodiments, the adaptor is connected to a medical monitor that was designed to work with wired sensors through a different connection than used for the wired sensors. For instance the adaptor may connect to the medical device through a USB or SDIO port. In these embodiments, the adaptor comprising the base-ASIC chip allows medical monitors designed for use with wired sensors to be used with wireless sensors with minimal or with no modification to the medical monitor.

In some embodiments, in addition to the patch-ASIC chip and the base-ASIC chip, the system further includes a gate-ASIC chip incorporated into a gate device. In some cases the gate-ASIC chip is attached to a μ-Gate, comprising a printed circuit board with an antenna attached to the printed circuit board. In some embodiments, the gate device acts as an intermediary (gateway), for instance, controlling communication between the base-ASIC chip and the patch-ASIC chip. The gate device is useful, for instance in circumstances where the patient wearing the wireless patch may be moved a distance away from the base-ASIC chip for relatively long time periods. In these situations, the gate-device, which will typically be small enough to, for example, be comfortably carried in a pocket, can communicate with the patch-ASIC chip while the patch-ASIC chip is out of communication range of the base-ASIC chip, continuing to monitor and/or control the functions of the patch, and collect and store data sent by the patch, and be able to forward that data to the μ-Base wirelessly. In general, in systems where one or more gate devices are present, patch devices communicate to the μ-Base via the gate device(s). This helps reduce the power consumption of the patch devices as they can transmit at lower power to communicate with the gate device(s) which are in closer proximity than the μ-Base itself.

In some embodiments the gate devices can be incorporated into patches. In these cases, the gate device can perform its gateway function, and can also perform as a patch by being connected (wired) to sensors and receiving physiological signals. For example, one system of the present invention has multiple patches, each patch comprising a patch-ASIC chip; and a gate device comprising a gate-ASIC chip incorporated into a patch on a patient. The gate device can communicate with the multiple patches on the patient, and the gate device can act as an intermediary between the patches comprising the patch-ASICs and a μ-Base comprising a base-ASIC. In one embodiment of this system, the patch-ASICs communicate only by UWB, while the gate-ASIC can communicate with the base-ASIC by either UWB or narrowband. This system allows the patches with patch-ASICs to operate at low power and to have low energy usage by transmitting only in UWB. In this embodiment, the gate-device may have a larger battery than the patches comprising the patch-ASIC chips. In some embodiments, the patch-ASIC chips used in this scenario can be made inexpensively due to the fact that the chips do not have multiple radios. In other embodiments, the patch-ASIC chip and the gate-ASIC chip used in this scenario are made as part of an ASIC superset, where the narrowband radio can be turned off on the patch-ASIC chip. The use of an ASIC superset chip can be advantageous where cost can be driven down by producing a higher volume of a single type of chip.

In other embodiments, the gate device acts mainly as a storage device for physiological information generated and transmitted by the patch. For example, the gate device can have a memory storage capability for storing data transmitted wirelessly from the patch to the gate device. In this embodiment, the gate need not send data wirelessly, and the stored data can be retrieved via a physical connection to another device. For example, the gate device may have a removable memory device, or the gate device may have a connector which allows it to be connected to another device in order to download the information on the gate device to another device, such as a medical device or computer.

One aspect of the invention is the management of power dissipation in a wireless monitoring system in a real environment such as in a hospital, where the patch-ASIC chip, the base-ASIC chip, and the gate-ASIC chip will end up at different distances from one another in different circumstances. For example, the power dissipation of the patch can be kept low by using low transmission power at the patch, and/or by using a transmitting in a mode, such as ultra-wideband (UWB) that uses less power. However, these power management solutions may only be successful if the receiving device is close enough to the sending device and has a sensitive enough receiving capability to reliably receive the signals. Thus in the present invention, the base-ASIC chip (and the μ-Base) generally have adequate power available to carry out more power and processor intensive functions, as the base-ASIC chip (and μ-Base) is typically deriving its power from either a plugged-n stationary device, or from a relatively large battery in a mobile or portable device; whereas the patch-ASIC chip must conserve its power because it is part of a patch which is generally small light, and inexpensive, and thus will only have a small battery with limited power and energy. The chips, patches, systems, and methods of the present invention provide for the base-ASIC chip, the μ-Base, to use its power, resources, and functionality to lower the power output requirements of the patch-ASIC chip, μ-Patch, and patch, thus extending the time over which the patch can transmit patient data without recharging or replacing the battery, and ensuring secure and reliable communication with low power dissipation.

Wireless Technology (Radio)

The devices, systems, and methods of the invention relate to the use of wireless technology. As used herein, the term "wireless" refers to any suitable method of communicating without the use of a hard-wired electrical connection. A hard-wired connection involves the direct physical connection of electrical conductors through which an electrical signal flows. The distances over which the wireless communication occurs may be short (a few meters or less) or long (kilometers or greater). The radio can be either ultra-wideband (UWB) radio or narrowband radio. Narrowband radio, as used herein, is any radio that is not ultra-wideband (UWB) radio. For example, the Federal Communications Commission (FCC) defines UWB as fractional bandwidth measured at −10 dB points where (f_high−f_low)/f_center>20% or total Bandwidth>500 MHz. Some examples of the narrowband radios suitable for the present invention are: Wi-Fi standard based radio, Bluetooth standard based radio, Zigbee standard based radio, MICS standard based radio, and WMTS standard based radio. Suitable wireless radio protocols include WLAN and WPAN systems.

ASIC Chips

The invention utilizes integrated circuits that are ASIC chips. An ASIC (Application Specific Integrated Circuit) is a system-on-chip semiconductor device which is designed for a specific application as opposed to a chip designed to carry out a specific function such as a RAM chip for carrying out memory functions. ASIC chips are generally constructed by connecting existing circuit blocks in new ways. The ASIC chips described herein are designed for the application of monitoring of physiological signals wirelessly. In some embodiments the ASIC chips of the invention comprise two or more ASIC chips that are designed to work together. In some embodiments, the ASIC chips of the present invention are made using a bulk CMOS process. In some embodiments, the ASIC chip of the present invention encompasses end-to-end functionality with the following features: Analog and digital sensor electronics for multi-sensor processing; a micro-controller based design to coordinate onboard resources and perform power-control; hardwired PHY and MAC coprocessors which enable highly integrated data-paths in small silicon-area, and a CMOS radio with built-in power amplifier.

In some embodiments, the ASIC chips comprise circuits for encryption and/or decryption, for advanced encryption standard (AES), cyclic redundancy check (CRC), and/or forward error correction (FEC).

The ASIC chips of the present invention are designed to receive a variety of types of physiological signals. For example, the ASIC chips of the invention can receive signals from ECG, EEG, EMG, SpO$_2$, tissue impedance, heart rate, accelerometer, blood glucose, PT-INR, respiration rate and airflow volume, UWB radar, pressure, physical movement, body fluid density, patient physical location, or audible body sounds.

One aspect of the invention is an ASIC chip that is designed to receive signals from multiple types of sensors. The capability of receiving different types of signals can be important for the economics of the ASIC chip for several reasons. For one, the cost per chip drops with volume, and making a chip that can be used in multiple applications allows for higher volumes and therefore lower cost. In some cases the capability of measuring multiple types of physiological signals is built into the ASIC chip, thus allowing the ASIC chip to be directly connected to sensors without external signal conditioning. In some embodiments, the ASIC chip of the present invention has a programmable analog processor inside to program the ASIC to accept multiple physiological signals.

One embodiment of the invention is an ASIC chip that is designed to receive electrical physiological signals without the need for external signal conditioning. One embodiment of the invention is an ASIC chip that is designed to receive any of ECG, EEG, EMG, SpO$_2$, tissue impedance, heart rate, and accelerometer signals without the need for external signal conditioning.

The patch-ASIC chip of the present invention has the functionality required to receive physiological signals from a sensor, to wirelessly transmit the signals to a base device and in some cases to control the functionality of the patch. The patch-ASIC generally comprises at least a sensor interface for measuring physiological signals, a processor for processing the signals into sensor data, memory for storing data relating to the signals, a radio for transmitting sensor data, and power management circuits for controlling power on the chip.

In some embodiments, the patch-ASIC is capable of receiving both analog and digital signals. In some embodiments, the patch-ASIC supports and can receive signals from both passive and active sensing. Active signals are signals that are created by injecting an output signal and measuring a response. Active signals include radio frequency signals, electrical, optical, and acoustic signals (such as for blood-oxygen, body-impedance, ultrasound, etc.).

The patch-ASIC generally has memory for storing physiological data derived from the measured physiological signals. The data stored in memory can be the data as received at the sensor, or the data that has been processed. In some embodiments, the data is processed before being stored. For example, in some embodiments, the data is filtered to remove noise from the sample before it is stored. In some embodiments, the ASIC has circuits for the manipulating the data from the physiological signals. For example, circuits include, but are not limited to, digital filtering of sensor waveforms, lossless compression of sensor waveforms, and parameter extraction to identify onset of a disease condition (such as identifying a particular type of arrhythmia). In some embodiments, different firmware is used to support different disease conditions. An advantage of disease condition parameter extraction is that it can considerably reduce the amount of data that needs to be transmitted to the µ-Base, thereby reducing the radio power-consumption. A tradeoff is the power consumed in performing the local processing and the increased silicon-cost in the form increased firmware memory or hardware processing circuitry.

The patch-ASIC also generally has power management circuits designed to control and minimize the energy used by the chip in carrying out its functions. Power management circuits include, but are not limited to, clock-gating and protocol-level active, sleep and standby modes.

One use of the memory on the patch-ASIC is the use of the memory as a buffer to allow the decoupling of the receiving of signals and the transmission of data. Memory allows the patch-ASIC chip, for example, to substantially continuously receive data, but to transmit the data at a later time as a burst. This allows for the use of less energy by lowering the amount of time spent transmitting.

One aspect of the patch-ASIC chip is its ability to be controlled by the base-ASIC chip. The patch-ASIC chip is able to receive and respond to instructions sent by the base device, such as instructions as to when to store data and when to transmit, instructions on power levels, and instructions on which radio mode to use (e.g. UWB or narrowband, or which narrowband frequency and protocol). In some embodiments, the patch-ASIC chip is designed only to have UWB radio in order to lower its power and energy output. A patch-ASIC with only UWB, and not narrowband radio capability can be useful in scenarios where the µ-Gate or µ-Base can be kept near the patch, for example, where the µ-Gate is incorporated into another patch on the same patient.

The patch-ASIC is generally incorporated into a µ-Patch. A µ-Patch comprises a printed circuit board (PCB) to which the patch-ASIC is attached. The PCB also has an antenna attached that is in electronic communication with the patch-ASIC through the circuit board. The circuit board may be rigid or flexible. The µ-Patch can also have additional components attached to the circuit board to enhance the functionality of the patch. For example, the µ-Patch can have a power amplifier for amplifying the signal from the patch-ASIC in order to increase the range of transmission by the antenna. The µ-Patch can also have additional memory chips attached to the circuit board to increase the memory storage capacity of the patch. In the case where the patch performs active sensing, the µ-Patch can have components attached to the circuit board that facilitate the output of signals. The µ-Patch can have a component that is separate from the patch-ASIC chip that performs digital signal processing (DSP). In some cases, the patch-ASIC chip can perform DSP, and the component that performs DSP enhances the DSP capability of the µ-Patch. In some cases, the patch-ASIC chip does not have DSP capability, and the component that performs DSP provides all of the DSP capability on the µ-Patch.

The base-ASIC chip of the present invention has the functionality for receiving data from the patch or the gate device, transmitting the data to a host device, and for controlling the functionality of the patch and/or the gate devices over the air. The base-ASIC generally has at least a processor for processing sensor data, memory for storing data relating to the signals, a radio for transmitting instructions to the patch-ASIC chip and to receive sensor data from it, power management circuits for controlling power on the chip, and a host interface allowing the base-ASIC chip to communicate with a host device. In some embodiments, the base-ASIC chip also has sensor inputs, allowing for some sensor signals to be directly received by the base device through a wired connection. The base-ASIC will generally have more processing power than the patch-ASIC or gate-ASIC, allowing the base-ASIC to perform more power and processor intensive functions. In some embodiments, the base-ASIC will have the ability to do significant signal processing and data analysis. In some embodiments, the base-ASIC will have the circuits for controlling the initialization and link set up, power management, data packet routing, type of transmission radio, radio transmit-power, radio receive-sensitivity, patch operational integrity, audio tone generation, display activation by the patch.

The base-ASIC is generally incorporated into a μ-Base (or MSP). A μ-Base comprises a printed circuit board (PCB) to which the base-ASIC is attached. The circuit board may be rigid or flexible. The circuit board generally also has an antenna that is in electronic communication with the base-ASIC through the circuit board. The μ-Base can also have additional components attached to the circuit board to enhance the functionality of the base device. The μ-Base is described in more detail below.

Some embodiments comprise a gate-ASIC chip. The gate-ASIC in some embodiments is incorporated into a gate device. The gate-ASIC chip has the functionality for receiving data wirelessly from one or more patches and for storing data in memory, and to forward the data wirelessly to the μ-Base. The gate-ASIC generally has at least a processor for processing sensor data, memory for storing data relating to the signals, a radio for communicating with the patch-ASIC chip, and power management circuits for controlling power on the chip.

The gate-ASIC is generally incorporated into a μ-Gate. A μ-Gate comprises a printed circuit board (PCB) to which the gate-ASIC is attached. The PCB also has an antenna that is in electronic communication with the gate-ASIC through the circuit board. The circuit board may be rigid or flexible. The μ-Gate can also have additional components attached to the circuit board to enhance the functionality of the base device. For example, the μ-Gate can have a power amplifier for amplifying the signal from the gate-ASIC in order to increase the range of transmission by the antenna. The μ-Gate can also have additional memory chips attached to the circuit board to increase the memory storage capacity of the gate device.

In some embodiments, the μ-Gate and the gate-ASIC chip can be incorporated into a patch. In these embodiments, the gate-ASIC chip will comprise a sensor interface for receiving physiological signals.

In most embodiments, the ASIC chip of the present invention, for example, the patch-ASIC chip, the gate-ASIC chip, or base-ASIC chip, comprise a single chip. In some embodiments, however, the ASIC chip can be physically on two chips. For instance, an ASIC chip may comprise memory functionality or power amplifier functionality that physically resides on a second chip but is used functionally as if it were part of a single ASIC chip.

In some embodiments, the patch-ASIC chip, the base-ASIC chip, and/or the gate-ASIC chip are manufactured as an ASIC superset wherein the functionality of all of the types of chips are on one chip, and the functionality that is not used on a given type of chip is turned off in that chip. For example, in some cases the patch-ASIC chip and the base-ASIC chip are made as a single ASIC superset wherein the base-ASIC chip has a high power narrowband radio that is turned off in the patch-ASIC chip.

In this application, we refer to a particular ASIC chip as communicating with another ASIC chip, as used herein communication with an ASIC chip is equivalent to there being communication through an ASIC chip, and generally means that data or information transferred from one ASIC chip reaches the other ASIC chip in some form. It is understood that the ASIC chips will generally communicate through antennae, and or other components.

Physiological Patch

The present invention relates to physiological patches for the measurement of signals relating to a physical parameter in a patient, and the transfer of data relating to the measured physical signals to a remote location. The patches of the present invention communicate wirelessly with a base device or with a gate device or both a base and a gate device.

In some embodiments, the patch includes one or more sensors incorporated into the patch. In other cases, the patch does not include sensors, but is connected to the sensor by wires, and receives physiological signals from the sensor through the wires. In some cases, the patch includes one or more sensors, and in addition, is connected by wires to other sensors that do not reside on the patch.

The patches of the present invention are generally wearable. In some cases they are held onto the skin with an adhesive. In some cases, for example, where an electrical signal is being measured, e.g. for ECG or EEG, some or all of the adhesive is electrically conducting, for example comprising silver and or silver chloride. In other cases, the adhesive is electrically non-conductive. The patch adhesive can be either wet or dry. In some cases, the patch can be held in place with straps or clips or may be incorporated into a piece of wearable clothing such as a hat, gloves, socks, shirt, or pants. In some cases, the patch is implanted. For multiple Patches, for example for EEG monitoring, the patches can be kept together (in sort of a shower-cap) so that they can be applied over the head together.

The patches may be placed on any suitable part of the body depending on the physiological signal and the condition to be measured. For ECG monitoring, for example, in some embodiments, a single patch can be used, the patch is placed on the upper-chest area. For EEG monitoring, e.g. for monitoring sleep Apnea, multiple patches are placed on the head.

The patches will generally be placed in direct contact with the body. This will be the case for embodiments in which electrical physiological signals are measured, and where the patch incorporates the sensor. In other embodiments, the patch is in proximity of the body, but not in direct contact. For example, there may be no need for direct contact for applications such as the measurement of $SpO_2$ where the patch may be placed next to a finger-tip assembly consisting of the LED/photodiode combination.

In some embodiments, the patch consists of the patch-ASIC, with multiple metal-electrodes (along with electrode-gel) on one side to pickup sensor signals from the body, and PCB trace antenna on the output side of the patch to radiate the radio (RF) signal. A suitable patch of this type of patch is described in co-pending U.S. Patent Application 60/940,072, and U.S. Patent Application 60/943,539, which are incorporated by reference herein in their entirety.

In some embodiments, the patch-ASIC has built-in sensor-signal processing for physiological signals such as ECG and EEG. In some embodiments, sensor-signal processing is provided by components within the patch, but not included on the ASIC. For example, circuitry such as analog amplification and filtering can be on the patch in separate components. The additional components can be used for example for active sensing applications such as blood-oxygen level (SpO2), which require outputs to drive light emitting diodes (LEDs, e.g. red/infra-red) whose light is usually passed through a finger-tip and captured by a photodiode and fed back to the ASIC for further processing. The finger-tip sensor-assembly (LEDs and photodiode) is generally not incorporated into the patch itself. There will generally be dedicated inputs/outputs on the patch to connect to this sensor assembly, and/or to similar sensor assemblies. Digital sensor signals can also be input to the Patch, and processed by the ASIC. One aspect of the invention is a patch that is capable of measuring ECG, EEG, EMG, $SpO_2$, tissue impedance, heart rate, accelerometer, blood glucose, PT-INR, respiration rate and airflow volume, UWB radar, pressure, physical movement, body fluid density, patient physical location, and audible body sounds. In some embodiments the patch comprises an ASIC that can measure ECG, EEG, EMG, $SpO_2$, tissue impedance, heart rate, and accelerometer signals without external signal conditioning.

In some embodiments, the patch is a cardiac patch that can measure all of ECG, $SpO_2$, tissue impedance, accelerometer, and PT-INR signals. In some embodiments, the patch is a neurological patch for measuring sleep apnea that can measure all of EEG, EMG, $SpO_2$, heart rate, respiration rate and airflow volume, and pressure signals. In some embodiments, the patch is an endocrinological patch for measuring diabetes/wound that can measure all of ECG, blood glucose, and UWB radar signals. In some embodiments, the patch is a fitness and wellness patch that can measure all of ECG, heart rate, accelerometer, and pressure signals.

In some embodiments, the patch includes a PCB antenna, battery, sensor-electrodes, as well as the electronics section comprising the μ-Patch with patch-ASIC and other electronic components. The electrodes section and electronics section are typically manufactured separately and assembled together, along with the battery. In some embodiments, the electrodes section is flexible, and the electronics section is semi-rigid or flexible. In some embodiments, both sections are mass produced, machine assembled and tested. The term "batteries" will generally be used herein but it is to be understood that generally another power source other than a battery could also be used.

The patches of the invention generally have a power source incorporated into the patch. The battery is electrically connected to the patch-ASIC chip. The power source can be any suitable power source. The power source is typically a battery such as Li-ion, NiCD, NiMH, or Zn-air battery. In some embodiments, the power source can be a source other than a battery, for example, an ultracapacitor, micro-fuel cell, micro-heat engine, or radioactive power source. Because the patch is generally meant to be worn, the battery should be small and light. In some cases, the battery is removably attached the patch. In some cases, the battery is substantially irreversibly attached to the patch, for example, soldered onto the PCB of the μ-Patch. In some cases the battery is rechargeable, for example magnetically rechargeable without electrical contact with the recharging device.

In some embodiments, the patch comprises an alert incorporated into the patch. The alert can provide the user, for example, with information about the state of the patch, the proper placement of the patch, the distance of the user from the base device, the state of the battery in the patch, or the time the user has been outside of a communication range with the base device. The alert can also be used to inform the user of a particular health condition or of a recommended action to take due to the measured physiological signals. For example, the alert can be used to recommend that the patient take a medication and/or to contact medical professionals. The alert can be, for example, audio, visual, or vibration based. In some cases, the alert is at the base or gate device. The audio alert can be, for example, a small speaker that either beeps or chimes to alert the user, or may have more complex audio output including using language to communicate with the user. A visual alert can be, for example, a flashing or constant light such as an LED, or can comprise a display that displays signals to the user, such as a liquid crystal display capable of displaying alpha-numeric characters.

In one embodiment, an alert on the patch (or on the base or gate) is used to provide confirmation of proper patch placement to the user at the time of patch placement. For example, the patch may monitor test signals to confirm correct placement. The confirmation of correct placement can be carried out in some cases by the patch, and in some cases with a combination of the base device and the patch, e.g. by holding the base device near the patch. An audio-alert at the Patch could be used for when a patient goes out of the effective range of a μ-Base.

In some embodiments, the patches of the present invention are disposable after use. For example, electrodes with wet/dry gel may be non-reusable once they are peeled-off the body, thus a patch comprising electrode sensors would generally be disposed of after use. In other embodiments, the patch is manufactured in a two-piece configuration such that the electrodes in one piece are disposable, but the μ-Patch with the patch-ASIC and associated electronics in another piece is reusable by connection to another electrode bearing piece.

It is generally desired that the patches be comfortable to wear, and thus the patches of the invention are typically small. In some embodiments the patches are relatively thin and flat, so as to be placed on the surface of the body. In some embodiments portions of the patch are flexible to conform to the body. In some embodiments, the patches are less than about 30 $cm^2$ in area. In some embodiments, the patches are less than about 20 $cm^2$ in area. In some embodiments, the patches are less than about 10 $cm^2$ in area. In some embodiments, the patches are less than about 5 $cm^2$ in area. In some embodiments, the patches are less than about 2 cm thick. In some embodiments, the patches are less than about 1 cm thick. In some embodiments, the patches are less than about 0.5 cm thick. In some embodiments, the patches are less than about 0.2 cm thick.

In some embodiments, the patches are less than about 30 $cm^2$ in area and less than about 1 cm thick. In some embodiments, the patches are less than about 20 $cm^2$ in area and less than about 1 cm thick. In some embodiments, the patches are less than about 20 $cm^2$ in area and less than about 0.7 cm thick. In some embodiments, the patch comprises electrodes for measuring ECG and is about 15 $cm^2$ to about 25 $cm^2$ in area and about 0.5 cm to about 1 cm thick.

In some embodiments, the patches have a volume of less than about 30 $cm^3$. In some embodiments, the patches have a volume of less than about 20 $cm^3$. In some embodiments, the patches have a volume of less than about 15 $cm^3$. In some embodiments, the patches have a volume of less than about 10 $cm^3$. In some embodiments, the patches have a volume of less than about 5 $cm^3$.

One aspect of the invention is a patch, used as part of a system that has relatively low volume as that described above but can monitor and transmit data for relatively long periods of time without having to replace or recharge the batteries.

In some embodiments, devices, systems and methods of the invention provide a patch that can wirelessly transmit data while monitoring a physiological signal from a patient for at least about 1, 2, 3, 4, 5, 6, 7, 8, 9, 10, 11, 12, 14, 17, 21, 28 or more than 28 days without changing or recharging the batteries. In some embodiments, the patch can wirelessly transmit data while substantially continuously monitoring a physiological signal from a patient for at least about 1, 2, 3, 4, 5, 6, 7, 8, 9, 10, 11, 12, 14, 17, 21, 28 or more than 28 days without changing or recharging the batteries.

As referred to herein, a patch is substantially continuously monitoring a physiological signal when it is sampling the physiological signal at regular intervals where the sampling rate is such that the physiological condition is effectively monitored over the time period. The frequency of sampling will depend on the particular physiological condition that is monitored, and the time frame during which a meaningful measurable event will occur. In some cases the appropriate rate can be determined by using the Nyquist rate. The Nyquist rate is the minimum sampling rate required to avoid aliasing, equal to twice the highest modulation frequency contained within the signal. In other words, the Nyquist rate is equal to the two-sided bandwidth of the signal (the upper and lower sidebands). For example, for measuring ECG signals, the relevant physiological signal information occurs at a rate of about 100 Hz, thus the sampling should be at a minimum of about 200 Hz. In some cases, it is prudent to sample at a rate higher than the Nyquist rate. In some embodiments of the invention, the physiological signal that is continuously monitored is an ECG measurement which is continuously sampled at a rate of 200 Hz to 800 Hz. In some embodiments of the invention, the physiological signal that is continuously monitored is an ECG measurement which is continuously sampled at a rate of 300 Hz to 500 Hz. In some embodiments of the invention, the physiological signal that is continuously monitored is an ECG measurement which is continuously sampled at a rate of about 400 Hz. The term substantially continuous includes situations where the measurement is interrupted for a fraction of the time of the measurement. For example a substantially continuous measurement would occur if the continuous measurement occurred over a substantial period of the time of measurement.

In some embodiments, the patch can wirelessly transmit data while monitoring a physiological signal from a patient for at least about 1, 2, 3, 4, 5, 6, 7, 8, 9, 10, 11, 12, 14, 17, 21, 28 or more than 28 days without changing or recharging the batteries where the battery in the patch with a type of battery that provides, on average, less than about 50, 100, 150, 200, 250, 300, 400, 600, 800, 1000, or 1200 mA-hours.

In some embodiments, the patch can transmit about 1, 2, 5, 10, 15, 20, 25, 30, 35, 37, 40, 50, 60, 75, 90, 100, 500 or more than 500 KB or 1, 2, 5, 10, 15, 20, 25, 30, 35, 37, 40, 50, 60, 75, 90, 100 or more than 100 MB of data per day while monitoring a physiological signal from a patient for at least about 1, 2, 3, 4, 5, 6, 7, 8, 9, 10, 11, 12, 14, 17, 21, 28 or more than 28 days without changing or recharging the batteries. In some embodiments, the patch can transmit about 5 MB of data per day while monitoring a physiological signal from a patient for at least about 2 days without changing or recharging the batteries. In some embodiments, the patch can transmit about 10 MB of data per day while monitoring a physiological signal from a patient for at least about 2 days without changing or recharging the batteries. In some embodiments, the patch can transmit about 20 MB of data per day while monitoring a physiological signal from a patient for at least about 2 days without changing or recharging the batteries. In some embodiments, the patch can transmit about 50 MB of data per day while monitoring a physiological signal from a patient for at least about 2 days without changing or recharging the batteries. In some embodiments, the patch can transmit about 5 MB of data per day while monitoring a physiological signal from a patient for at least about 4 days without changing or recharging the batteries. In some embodiments, the patch can transmit at least about 20 MB of data per day while monitoring a physiological signal from a patient for at least about 7 days without changing or recharging the batteries. In some embodiments, the patch can transmit at least about 20 MB of data per day while monitoring a physiological signal from a patient for at least about 14 days without changing or recharging the batteries.

In some embodiments, the patch can transmit at least about 1, 2, 5, 10, 15, 20, 25, 30, 35, 37, 40, 50, 60, 75, 90, 100, 500 or more than 500 KB or 1, 2, 5, 10, 15, 20, 25, 30, 35, 37, 40, 50, 60, 75, 90, 100 or more than 100 MB of sensor data per day at a range of up to about 30 m while monitoring a physiological signal from a patient for at least about 1, 2, 3, 4, 5, 6, 7, 8, 9, 10, 11, 12, 14, 17, 21, 28 or more than 28 days without changing or recharging the batteries. In some embodiments, the patch can transmit at least about 5 MB of sensor data per day at a range of up to about 30 m while monitoring a physiological signal from a patient for at least about 2 days without changing or recharging the batteries. In some embodiments, the patch can transmit at least about 10 MB of sensor data per day at a range of up to about 30 m while monitoring a physiological signal from a patient for at least at least about 2 days without changing or recharging the batteries. In some embodiments, the patch can transmit at least about 20 MB of sensor data per day at a range of up to about 30 m while monitoring a physiological signal from a patient for at least about 2 days without changing or recharging the batteries. In some embodiments, the patch can transmit at least about 50 MB of sensor data per day at a range of up to about 30 m while monitoring a physiological signal from a patient for at least about 2 days without changing or recharging the batteries. In some embodiments, the patch can transmit at least about 10 MB of sensor data per day at a range of up to about 30 m while monitoring a physiological signal from a patient for at least about 4 days without changing or recharging the batteries. In some embodiments, the patch can transmit at least about 10 MB of sensor data per day at a range of up to about 30 m while monitoring a physiological signal from a patient for at least about 7 days without changing or recharging the batteries. In some embodiments, the patch can transmit at least about 10 MB of sensor data per day at a range of up to about 30 m while monitoring a physiological signal from a patient for at least about 14 days without changing or recharging the batteries.

In some embodiments, the patch uses less than about 1, 2, 3, 4, 5, 6, 7, 8, 9, 10, 15, 20 mW of power on average. In some embodiments the patch has a volume that is less than about 20, 30, 40, 50, or 60 cm$^3$ and uses less than about 1, 2, 3, 4, 5, 6, 7, 8, 9, 10, 15, 20 mW of power on average. In some embodiments, the patch has a volume that is less than about 30 cm$^3$ and uses less than about 10 mW on average. In some embodiments, the patch has a volume that is less than about 30 cm$^3$ and uses less than about 6 mW on average. The volume of the patch can be calculated in some cases, for example, where the patch is in the shape of a disk, by multiplying the area of the patch by the thickness of the patch.

The term "sensor data" is used to describe the amount of data transmitted from the patch to the μ-Base. In this context sensor data means the data that is sent from the patch that directly correlates with the physiological signal and excludes data sent, for example as part of an encryption scheme.

Base Device (μ-Base)

One aspect of the invention is the base device which comprises a μ-Base which includes a base-ASIC chip. The base-ASIC is generally incorporated into a μ-Base (or MSP). A μ-Base comprises a printed circuit board (PCB) to which the base-ASIC is attached. The circuit board may be rigid or flexible. The circuit board generally also has an antenna that is in electronic communication with the base-ASIC through the circuit board. The μ-Base can also have additional components attached to the circuit board to enhance the functionality of the base device. The μ-Base receives sensor data from one or more patches and or gate devices. The μ-Base generally processes the sensor data, and sends the processed sensor data to a host device. In addition, the μ-Base controls functions of the patch including supervising power management and controlling data flow.

The host device is a device which can host a μ-Base module. In some embodiments, the μ-Base is incorporated into host device, and can for example, be fully integrated within the host. The base-ASIC can be soldered onto a board within a host device such as mobile medical monitor which provides power to the base-ASIC chip and may provide other functionality such as an antenna. In some embodiments, the μ-Base can be either connected to the host as an external device via a host interface bus. In some embodiments, the μ-Base is incorporated into a device, such as a card that connects with the host device. In some embodiments, the μ-Base is incorporated into an adaptor which connects to the host device. The μ-Base adaptor can connect to the host device by any suitable input or input/output port. In some embodiments, the μ-Base connects to the host device through a serial port with an interface such as USB or SDIO.

The host devices can be any suitable stationary, portable, or mobile device or a stationary, portable, or mobile medical instrument. Examples of host devices include a cellular phone, pager, i-Pod™, PDA, watch, or other mobile device, laptop, notebook, palm-top, or desk-top computer, or a medical instrument. Suitable medical instruments include medical instruments for monitoring health conditions by measuring physiological signals such ECG, EEG, EMG, $SpO_2$, tissue impedance, heart rate, accelerometer, blood glucose, PT-INR, respiration rate and airflow volume, UWB radar, pressure, physical movement, body fluid density, patient physical location, or audible body sounds. The medical instrument can be stationary, desk-top, portable, or mobile.

One aspect of the invention involves using a μ-Base incorporated into an adaptor in order to allow a medical instrument designed to measure sensor data through wired connections to measure similar sensor date through a wireless connection. This allows for conversion of a wired-sensor medical device into a wireless sensor medical device. In some embodiments, the adaptor connects to the medical device through the same connectors to which the wired sensors were connected. In other cases, the μ-Base adaptor connects to the medical device through another port on the medical device. For example, where a medical device was designed to measure pulse-rate with wired sensors that connect directly into the medical device, the μ-Base adaptor could plug into the jacks into which the wired sensors are designed to be connected. In this case, the μ-Base would receive the wireless signal from the μ-Patch, convert the signal if needed and send the signal to the medical instrument. Alternatively, the μ-Base adaptor could be made to plug into another port such as a USB port on the medical instrument. In this case, the μ-Base would convert the wireless signals from the μ-Patch into signals appropriate for transmission via this port. The μ-Base adaptor form-factor depends on the host-device as well as application. It can be, for example of USB-stick or mini-SD.

In some embodiments, the μ-Base will derive its power from the host device. In some embodiments, the μ-Base will have associated power sources such as batteries. The μ-Base will generally have more energy available to it than the μ-Patch. The present invention allows for the μ-Base to perform the more power and processor intensive functions, conserving the energy usage of the μ-Patch.

One aspect of the invention is the utilization of the μ-Base as a master device, where the μ-Base can test, control, and monitor the functions of μ-Patches and/or μ-Gates by sending and/or receiving test signals and/or control signals. Examples of functions that are controlled by the μ-Base include initialization and link set up, power management, data packet routing, type of transmission radio, radio transmit-power, radio receive-sensitivity, patch operational integrity, audio tone generation, display activation, or a combination thereof.

In some embodiments, a network made up of the μ-Base, μ-Patch(es), and μ-Gate(s) work on a packet-data protocol. Using this network, μ-Base keeps track of the link-quality of various wireless links between the μ-Base, μ-Patch(es), and μ-Gate(s) and takes corrective actions as needed. For example, if the link from a μ-Patch to one of the μ-Gate degrades too much, the μ-Base can send a command to the μ-Patch to switch its link to a standby μ-Gate for better link quality.

In some embodiments, the μ-Base can instruct the μ-Gate to switch from a UWB radio to narrowband radio depending on certain signal quality parameters. In the absence of strong narrowband interference, for instance, UWB link is used. When strong narrowband interference is detected (thereby degrading link quality), a narrowband link is used with a different narrowband carrier until the narrowband interferer disappears. The link is then switched back to UWB. This scheme results in lower overall power consumption because UWB radio consumes less power. Systems for wireless communication using multiple radios is described in co-pending U.S. Patent Application 60/894,174, U.S. Patent Application 60/894,093, and U.S. Patent Application 60/943,540 which are incorporated by reference herein in their entirety.

In some embodiments, the μ-Base can also control μ-Patch transmit power by issuing commands to reduce/increase transmit power depending on the receive signal strength. This helps save energy and provides higher reliability. The μ-Base can also issue commands to μ-Patch(es) to go into sleep-modes to conserve power.

In some embodiments, the μ-Base sends periodic commands to instruct μ-Patch(es) to transmit data. Implementing the power-control algorithms on the μ-Base helps simplify the μ-Patch implementation, reducing cost and power.

In some embodiments, the μ-Base performs duty-cycle control. For example, the μ-Base performs clock-gating with protocol-level sleep modes to reduce power dissipation. For example, during RF transmission, the receive-section is turned off and during RF reception, the transmit-section is turned off. During silent periods, only the front-section of the radio receive-chain stays on to listen for packets meant for the particular Patch, and wakes-up the rest of the receiver when it detects them.

In some embodiments, the μ-Base performs functional allocation on the μ-Patch, and/or μ-Gate. The μ-Base can dynamically alter the performance of the functional blocks. For example, receiver sensitivity and transmit phase-noise can depend on the biasing of the RF circuitry, which in turn affects power-consumption. When a transmitter is nearby, the receiver doesn't need high sensitivity, so it can reduce it by reducing the bias, saving power. Similarly, in a low interference environment, higher phase-noise could be tolerated, saving power. In addition, lower energy use by the patch is achieved by using asymmetric schemes that require more powerful coding and modulation schemes with more complex receive processing on the μ-Base, while requiring simple transmit-processing on the μ-Patch. More powerful receive processing on the μ-Base include, for example turbo-decoding (forward error-correction) and smart-antenna schemes. These schemes lessen the burden for the μ-Patch to transmit high-power to maintain a reliable communication-link, thus saving energy. Suitable smart antenna schemes are described in co-pending U.S. Patent Application 60/943,538 which is incorporated by reference herein in its entirety. The smart antenna schemes can use beam-forming techniques, and can involve data processing to enhance signal to noise. In some embodiments, the smart antenna scheme on the μ-Base comprises more than one antenna. In some embodiments, the smart antenna scheme on the μ-Base comprises two or more antennae. In some embodiments, the smart antenna scheme on the μ-Base comprises 4 or more antennae. In some embodiments, the smart antenna scheme on the μ-Base comprises 2, 3, 4, 5, 6, 7, 8, 12 or more than 12 antennae. In some embodiments, the smart antenna scheme on the μ-Base comprises about 4 antennae.

In some embodiments, the μ-Base performs authentication of patches at the time of their placement on the body and their initialization. By bringing the μ-Patch close to the μ-Base at the time of placement, private user-specific key can be transferred from the μ-Base to the μ-Patch. In some cases, by being close to the μ-Patch, the μ-Base can transmit the key at very low-power so that other devices cannot listen to the key transmission. By using this active authentication/initialization process by the μ-Base, long sequences of μ-Patch discovery and authentication similar to generic wireless networks is avoided, thereby saving power.

In some embodiments, the patch-ASIC on the μ-Patch comprises an encoding scheme for encoding transmission, and the base-ASIC chip on the μ-Base comprises both an encoding scheme and a decoding scheme, wherein the decoding scheme on the μ-Base is more power and processor intensive than the encoding scheme on the μ-Patch. In some embodiments, the encryption scheme uses shared keys, wherein the device comprising the base-ASIC chip wirelessly writes the shared keys to the patch. In some embodiments, the patch-ASIC chip has a simple turbocode encoder, and the base-ASIC chip has the more complex turbocode decoder. In some embodiments, the encryption scheme is an Advanced Encryption Standard (AES) scheme, where the decryption part of the scheme resides on the base-ASIC chip.

Gate Device (μ-Gate)

One aspect of the invention is the gate device which comprises a μ-Gate which includes a gate-ASIC chip. The gate device is generally a small portable device that can easily be kept on or near the user. For example, the gate device can be of the size that can be comfortably kept in a pocket. In some embodiments, the gate device could have, for example, the area of a credit card, about 2 inches by about 3 inches, and less than about 0.5 inches thick. In some cases, the gate device can act as an intermediary device between the μ-Base and the μ-Patch. In other cases, the gate device can act primarily as a memory storage device, to store data transmitted by the patch. In some embodiments, the μ-Gate can be incorporated into a patch where it can act as a higher performance patch where it can perform physiological sensing functions like a regular patch comprising a patch-ASIC. For example, the patch comprising the μ-Gate can act as a gateway for multiple other patches on the same patient. The patch comprising the μ-Gate can, for example, have the capacity to communicate in either UWB or narrowband with the μ-Base, and may have a larger memory capacity and a larger battery than the other patches. The other patches comprising patch-ASICs can operate at lower power by, for example communicating only by UWB with the μ-Gate which will always be close to the patches if placed on the same patient. The μ-Gate, however, will have the capacity to manage communication with the μ-Base, which may sometimes be farther away from the μ-Gate, necessitating, for example communication by narrowband which requires more power and energy and/or the storage of larger amounts of data on the μ-Gate. The μ-Gate can collect data from other patches to send to a μ-Base.

For example, in a system with multiple patches, the gate devices are introduced to aggregate the μ-Patch sensor data (wirelessly) and then transmit it to the μ-Base (essentially acting as gateways). This allows the μ-Patches to spend much less energy to reliably transmit data to an on-body or nearby μ-Gate device as opposed to a μ-Base device that could be tens of meters away. In some cases a redundant (standby) μ-Gates is used for reliability in case the primary μ-Gate is unreachable by either μ-Patches or μ-Base. The standby μ-Gate can also be used as load-balancer and data backlog remover when links of multiple patches to the primary μ-Gate degrade temporarily, and there is a need to catch up with clearing the buffered data in Patches by sending it to the μ-Base using both primary and secondary μ-Gates.

One aspect of the invention is a system for monitoring physiological signals comprising two or more ASIC chips wherein the chips are designed to work together to measure physiological signals, comprising: (a) a patch-ASIC chip for incorporation into a physiological signal monitoring patch comprising a sensor interface for measuring physiological signals, a processor for processing the signals into sensor data, memory for storing data relating to the signals, a radio for transmitting sensor data, and power management circuits for controlling power on the chip; and (b) a base-ASIC chip comprising a processor for processing sensor data, memory for storing data relating to the signals, a radio for transmitting instructions to the patch-ASIC chip, power management circuits for controlling power on the chip, and a host interface allowing the base-ASIC chip to communicate with a host device. Generally the base-ASIC chip is incorporated into a μ-Base and the patch-ASIC chip is incorporated into a μ-Patch, wherein both the μ-Base and the μ-Patch comprise a printed circuit board and an antenna attached to the printed circuit board for transmitting radio signals.

In some embodiments, the base-ASIC acts as a master device to control a function of the μ-Patch or the μ-Gate or both the μ-Patch and the μ-Gate. Examples of functions controlled by the base-ASIC are initialization and link set up, power management, data packet routing, type of transmission radio, radio transmit-power, radio receive-sensitivity, patch operational integrity, audio tone generation, display activation, or a combination thereof.

Figure 7:
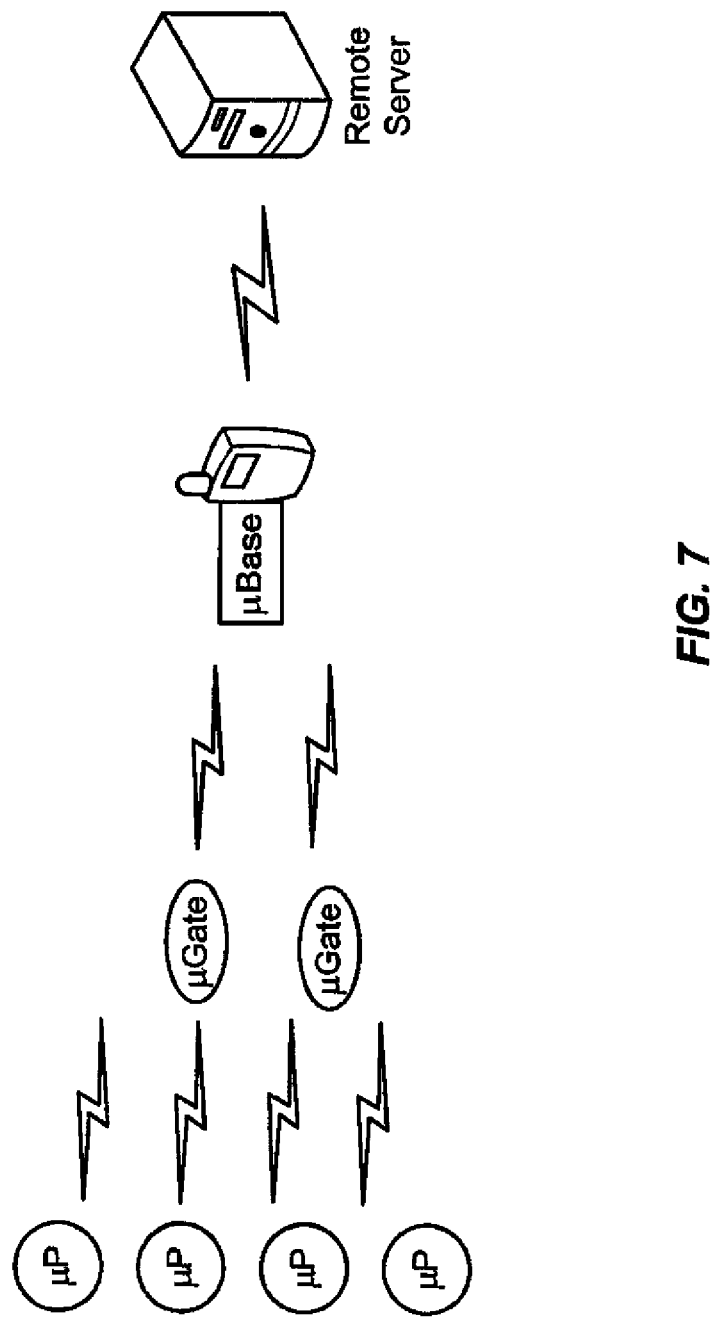
FIG. 7 illustrates a system of the present invention including µ-Patches, µ-Gates, and a µ-Base incorporated into a host device.

FIG. 7 shows an exemplary system that includes a μ-Gate. The system has multiple μ-Patches (μP) that are placed on the body of a patient. The system has a μ-Base, which in this embodiment is shown as being incorporated into a host device in the form of a cellular phone or PDA. The μ-Base can be incorporated either directly as an integral part of the host device or as part of an adaptor, such as a card that plugs into the host device. The system depicted has more than one μ-Gate that can communicate with the μ-Patches. In the system shown in FIG. 7, the μ-Gates are acting as intermediary devices that receive data from the μ-Patches and send data to the μ-Base. In addition, in some embodiments, the μ-Gates can receive and relay instructions from the μ-Base to the μ-Patches. In some cases, multiple μ-Gates can be used to provide a backup for receiving information from the μ-Patches, either to enhance the communication link by using, for example, the closest μ-Gate, or by enhancing the utilization of memory capacity. FIG. 7 shows that the system may also have an optional remote server which receives information related to the sensor data from the host device. In some cases, the remote server is a secure server that has other patient data to which the data from the host device can be added.

In some embodiments the host-device further communicates with a secure server to which information derived from the physiological sensors is transmitted. The transfer of information from the host device can be wireless, or by direct wired connection. Connection to the remote-monitoring server from the μ-Base or host-device would depend on the type of network connection the host-device has. It could be Wi-Fi (WLAN), cellular-data (GPRS/3G-CDMA), wired LAN/WAN (Ethernet/DSL/Cable), or wireless broadband WAN (WiMax). The secure server can, for example, integrate the information from the host device with other patient information.

The system of the present invention allows for the reliable and secure transmission of information related to a patient's condition. Reliability is the ability to transfer information accurately. In some embodiment, reliability is enhanced through schemes to make the wireless link reliable; for example by forward error-correction, packet-retransmission (automatic repeat-request or ARQ) and smart-antenna techniques on the receiver side. Retransmission requires buffering of data on the transmit side (as well as on the receive side when packets are received out of sequence). Interference from other users wearing similar patches is avoided by either frequency-hopping their carrier-frequencies in a pseudo-random fashion, or modulating their data with different pseudo-random code sequences with low cross-correlation properties.

Security relates to the ability of the system to keep the contents of the wireless transmission indecipherable to the third-party. In some embodiments of the invention, security is enhanced through encryption such as 128-bit AES (Advanced Encryption System) encryption. Packets are encrypted on the transmit side and decrypted on the receive side using a set of shared-keys. In one embodiment, the base device wirelessly writes these keys to the patch during initialization by placing the μ-Base and μ-Patch next to each other to prevent third-party listening. The keys can be made unique by virtue of unique ID's associated with each user.

The systems of the invention include continuous, periodic, or episodic measurement of a physiological condition. For example, one embodiment of a continuous monitoring scheme is a wireless Holter monitor. A Holter monitor is a portable device for continuously monitoring the electrical activity of the heart, typically for 24 hours or more. Its extended recording period is sometime useful for observing occasional cardiac arrhythmias that would be difficult to identify in a shorter period of time. For patients having more transient symptoms, a cardiac event monitor which can be worn for a month or more can be used. The Hotter monitor of the present invention records electrical signals from the heart via a one or more patches, each comprising μ-Patch with a patch-ASIC. The patches have electrodes that are typically attached to the chest. The number and position of patches with electrodes can vary, for example from one to eight. The patches monitor the electrical signals from the patient and transmit the sensor data to a μ-Base that is in a device that is kept on the patient, for example attached to a belt or kept in a pocket and is responsible for keeping a log of the heart's electrical activity throughout the recording period. The systems of the invention can perform episodic monitoring, in which a particular event is detected, either manually or automatically. An example of episodic monitoring is a cardiac event-monitor. In episodic monitoring, the μ-Base can control the μ-Patch, so that the patch performs only minimal sensor signal processing to detect the particular event, then monitors and stores physiological signals after event detection. The radio-section of the Patch would generally be turned off while waiting for the event. The systems of the present invention can also perform periodic monitoring wherein the μ-Patch measures and stores data related to physiological signals at a given time interval. In some embodiments, the μ-Base keeps track of the time intervals and instructs the μ-Patch when to measure signals and store data. Examples of periodic monitoring by the system of the present invention are blood-pressure or blood-glucose-monitoring. The time period between monitoring intervals for periodic monitoring can be from seconds to days. Generally, the time period between monitoring intervals for periodic monitoring is on the order of minutes to hours. For example, periodic monitoring for blood pressure could be every 10 to 30 minutes, and periodic monitoring of blood glucose could be every few hours.

In some embodiments, the systems of the present invention can be used in stand-alone mode. In stand alone mode a μ-Patch or μ-Gate will monitor and record sensor signals and store sensor data in a local memory. Once the observation period is completed, the stored data is transferred to a server-type machine for further analysis.

Asymmetric Distribution of Processing

One aspect of the invention relates to systems and methods in which the processing is distributed unequally or asymmetrically over different chips that are designed to work together. In some embodiments, the asymmetric system incorporates one or more patch-ASIC chips and a base-ASIC chip. In other embodiments the system also incorporates one or more gate-ASIC chips. All of these chips are designed to work together. In general, the system is designed such that the base-ASIC chip has more processing resources and therefore carries out more processing than the patch-ASIC chip or the gate-ASIC chip. In some embodiments, the base-ASIC chip will take on most or all of the processing of a certain type, allowing the system to function such that the patch-ASIC and/or gate-ASIC can function effectively using less energy, allowing them to run on small batteries for long periods of time without having to replace or recharge the batteries or replace the patch or gate.

In one aspect, the base-ASIC chip has more resources to implement the physical layer of the basic radio than the patch-ASIC chip. The resources devoted to the physical layer of the base radio include: the baseband signal processor, the data encoder/decoder, and the radio frequency transceiver. In some cases, the base-ASIC chip has more resources to implement media access control (MAC) functions that allows data interface to the radio's physical layer than does the patch-ASIC chip. In some cases the base-ASIC chip has more resources to run algorithms to monitor the radio environment and facilitate the coordination of multiple radios than the patch-ASIC does. In some cases the base-ASIC chip has more resources for multiple antenna signal processing to increase the link reliability than does the patch-ASIC chip. In some cases, the base-ASIC chip has more resources to supervise the proper functioning of the overall radio link and network than the patch-ASIC chip. In some cases the base-ASIC chip has more resources for power management than the patch-ASIC chip.

In some embodiments, the base-ASIC chip has more processing resources for one of the types of processing resources described above. In some embodiments, the base-ASIC chip has more processing resources for to 2, 3, 4 or more of the types of resources described above than the patch-ASIC chip. In some embodiments, the base-ASIC chip has more processing resources for all of the types of resources described above. For example, in some cases, the base-ASIC chip has more resources to implement the physical layer of the basic radio, more resources to implement media access control (MAC) functions that allows data interface to the radio's physical layer, more resources to run algorithms to monitor the radio environment and facilitate the coordination of multiple radios, more resources for multiple antenna signal processing to increase the link reliability and more resources to supervise the proper functioning of the overall radio link and network than the patch-ASIC chip.

In some embodiments, the base-ASIC chip has more processing resources than the patch-ASIC chip because the base-ASIC chip has higher complexity radio receivers and transmitters than those in the patch-ASIC chip. A typical radio transmitter or receiver generally contains three primary functions: Data Codec (Coder/Decoder), Baseband signal processor, and Radio Frequency (RF) transceiver. In some embodiments the base-ASIC chip has higher more processing power in one, two, or all three of these functions than the patch-ASIC chip. As used herein, a Data Codec (Coder/Decoder) refers to the encoding of data to be transmitted on the transmitter side to increase the system reliability. One example of Data Codec is Turbo coding. Correspondingly, the received data on the receiver side is decoded, for example, with a Turbo Decoder. A baseband signal processor performs various functions such as modulation/demodulation, equalization, and timing recovery. On the transmitter side, a carrier wave is modulated using a chosen scheme (e.g. QAM, BPSK) to produce a baseband signal for the transmission. The receiver performs corresponding demodulation functions on the received baseband signal. In addition the receiver performs various other functions such as equalization. A radio frequency (RF) transceiver transmits and receives radio signals. The RF transmitter can modulate a RF carrier wave with baseband signal for transmission through an antenna (up-conversion). Simpler transmitters, generally used on the patch-ASIC chip, can perform the up-conversion in one step and complex schemes, such as those employed on the base-ASIC chip, may include multiple steps with intermediate frequencies. On the receiving end, the reverse process takes place—down-conversion of the RF signal to baseband signal.

In addition, the radio can optionally contain additional blocks. For example, the radio may contain a processor to monitor the radio environment and coordinating the functionality of radios, a multiple antenna signal processor, and power control. These blocks can reside on the transmitter side, the receiver side or distributed on both sides. For the systems and methods of this invention, these blocks are generally contained mostly or substantially completely on the base-ASIC chip.

The low complexity transmitter utilized on the patch-ASIC chip performs the minimum needed functions form the above using simple circuits. The patch-ASIC chip/base-ASIC chip system is designed in order to push the complexity to the corresponding receiver on the base-ASIC chip, making its functions more complex (high complexity receiver). In this case, the silicon area of the transmitter will be much smaller than the corresponding receiver. The same strategy is applied to a pair of ASIC chips having high complexity transmitter and a low complexity corresponding receiver. The strategy also applies to a pair of high complexity and low complexity transceivers (combined transmitter/receiver). For example, in some embodiments, on one side, there is a low-complexity transceiver, and on the other side, there can be corresponding high complexity transceiver.

In some embodiments, Turbo encoding is performed on the patch-ASIC chip, while turbo decoding is performed on the base-ASIC chip. Typically, a turbo encoder complexity is exceedingly low compared to that of a turbo decoder. A turbo encoder typically encodes a data stream using two or more block or convolutional encoders, and transmitting the coded bits in a multiplexed fashion. One of the encoders encodes the data stream directly, while the other encoders first interleave the data stream before encoding it. The encoded bit streams are sometimes punctured by throwing away certain bits before being multiplexed and transmitted. This is done to meet channel data rate and bandwidth requirements.

The turbo decoder on the base-ASIC chip performs the inverse function of a turbo encoder by decoding the received data stream to recover the original data stream that is encoded on the transmit side. In the process of decoding, the decoder is able to correct errors introduced due to poor channel quality (fading, noise and interference) during transmission. The turbo decoder usually operates on soft-decision received bits, and iteratively decodes the coded bits from each of the encoders, while feeding channel quality information from one decoder (corresponding to one encoder) to the other decoder (corresponding to the other encoder). The turbo decoder typically uses a MAP (maximum a posteriori) algorithm as part of the decoding process. At each successive iteration, the additional channel quality information from one decoder helps decode the encoded stream with the other decoder in a more reliable fashion. At the end of a few iterations when high-level of reliability is achieved, hard-decision bits corresponding to the original data stream (input to the encoders on the transmit side) are recovered. In the process of decoding, the turbo decoder performs several stages of de-interleaving and re-interleaving of the received and recovered data streams. Turbo encoding and decoding is described in C. Berrou, A. Glaviex, and P. Thitimajshima, *IEEE Int. Conf. Commun.*, vol. 2, Geneva, Switzerland, May 1993, pp. 1064-1070, and B. Vucetic, J. Yuan, Kluwer Academic Publishers, 2000.

One aspect of the invention is a system comprising a base-ASIC chip and a patch-ASIC chip designed to work together wherein the base-ASIC chip has more silicon area than the patch-ASIC chip. The silicon area of the base-ASIC chip is larger, in general, because the base-ASIC chip has more processing capability as described herein. In some cases the higher silicon area of the base-ASIC chip is due, in large part, to the higher amount of processing resources for the radio core on the base-ASIC chip. In some embodiments, the ratio of the area of the base-ASIC chip to the area of the patch-ASIC chip is greater than about 1.5. In some embodiments, the ratio of the area of the base-ASIC chip to the area of the patch-ASIC chip is greater than about 2. In some embodiments, the ratio of the area of the base-ASIC chip to the area of the patch-ASIC chip is greater than about 3. In some embodiments, the ratio of the area of the base-ASIC chip to the area of the patch-ASIC chip is greater than about 4. In some embodiments, the ratio of the area of the base-ASIC chip to the area of the patch-ASIC chip greater than about 5. In some embodiments, the ratio of the area of the base-ASIC chip to the area of the patch-ASIC chip greater than about 10. In some embodiments, the ratio of the area of the base-ASIC chip to the area of the patch-ASIC chip is greater than about 1.5, 2, 3, 4, 5, 6, 8, 10, 12, 15, 20, or greater than 20. In some embodiments the ratio of the area of the base-ASIC chip to the area of the patch-ASIC chip is in a range of about 1.5 to about 3. In some embodiments the ratio of the area of the base-ASIC chip to the area of the patch-ASIC chip is in a range of about 2 to about 3. In some embodiments the ratio of the area of the base-ASIC chip to the area of the patch-ASIC chip is in a range of about 2 to about 5. In some embodiments the ratio of the area of the base-ASIC chip to the area of the patch-ASIC chip is in a range of about 3 to about 8. In some embodiments the ratio of the area of the base-ASIC chip to the area of the patch-ASIC chip is in a range of about 4 to about 8.

The absolute area of the silicon will depend, for example, on the type of processing which is used. For example, for 0.13 micron CMOS processing, the patch-ASIC chip can have a silicon area of, e.g. of 2 mm², 4 mm², or 9 mm², while the base-ASIC chip can have a silicon area of, e.g. 4 mm², 9 mm², or 16 mm².

The silicon area can be readily measured by measuring the geometric (two dimensional) area of the ASIC chip. For a rectangular chip, the area can be calculated by multiplying the length of the height and width (not the depth) of the chip. For a chip with irregular dimensions, the area can be easily be determined by one of skill in the art.

One aspect of the invention is a method comprising a base-ASIC chip and a patch-ASIC chip designed to work together wherein the base-ASIC chip dissipates more power than the patch-ASIC chip. An aspect of the invention is a method comprising: monitoring a physiological condition using two or more ASIC chips and a host device wherein the chips are designed to work together to measure physiological signals comprising: (a) receiving signals from a sensor at a patch-ASIC chip that is incorporated into a physiological signal monitoring patch, the patch-ASIC chip comprising a sensor interface coupled to the sensor, a processor coupled to the sensor interface, a memory element coupled to the processor, a radio coupled to the memory element; (b) transmitting data signals from the radio on the patch-ASIC chip through an antenna incorporated into the patch; (c) receiving the data signals at a base-ASIC chip comprising an antenna that sends the signals to a processor that processes data signals, a memory element coupled to the processor, a radio coupled to the memory element, and a host interface through which the base-ASIC chip communicates with a host device; and (d) transmitting instructions wirelessly from the base-ASIC chip to the patch-ASIC chip; wherein the base-ASIC chip consumes more power than the patch-ASIC chip. Power is energy transferred per unit time. Power is an instantaneous value, while Energy relates to the amount of power used over time. Thus, when the power dissipated by a chip of the present invention, the power dissipation is generally measured over a period of time, in which case, for example, the average power over that time period can be determined. When calculated in this way, the ratio of average power over time or the ratio of energy dissipated can be used. The power dissipation of the base-ASIC chip is larger, in general, because the base-ASIC chip has more processing capability as described herein.

In some cases the higher power dissipation of the base-ASIC chip is due, in large part, to the higher amount of processing resources for the radio core on the base-ASIC chip. In some embodiments, the ratio of the power dissipation of the base-ASIC chip to the power dissipation of the patch-ASIC chip is greater than about 1.5. In some embodiments, the ratio of the power dissipation of the base-ASIC chip to the power dissipation of the patch-ASIC chip is greater than about 2. In some embodiments, the ratio of the power dissipation of the base-ASIC chip to the power dissipation of the patch-ASIC chip is greater than about 3. In some embodiments, the ratio of the power dissipation of the base-ASIC chip to the power dissipation of the patch-ASIC chip is greater than about 4. In some embodiments, the ratio of the power dissipation of the base-ASIC chip to the power dissipation of the patch-ASIC chip greater than about 5. In some embodiments, the ratio of the power dissipation of the base-ASIC chip to the power dissipation of the patch-ASIC chip greater than about 10. In some embodiments, the ratio of the power dissipation of the base-ASIC chip to the power dissipation of the patch-ASIC chip is greater than about 1.5, 2, 3, 4, 5, 6, 8, 10, 12, 15, 20, or greater than 20. In some embodiments the ratio of the power dissipation of the base-ASIC chip to the power dissipation of the patch-ASIC chip is in a range of about 1.5 to about 3. In some embodiments the ratio of the power dissipation of the base-ASIC chip to the power dissipation of the patch-ASIC chip is in a range of about 2 to about 3. In some embodiments the ratio of the power dissipation of the base-ASIC chip to the power dissipation of the patch-ASIC chip is in a range of about 2 to about 5. In some embodiments the ratio of the power dissipation of the base-ASIC chip to the power dissipation of the patch-ASIC chip is in a range of about 3 to about 8. In some embodiments the ratio of the power dissipation of the base-ASIC chip to the power dissipation of the patch-ASIC chip is in a range of about 4 to about 8. The ratios are generally measured when the patch-ASIC chip and base-ASIC chip are in communication. In some embodiments the ratios are measured while the patch-ASIC chip and base-ASIC chip are in continual data transmission.

The absolute amount of power dissipated or energy used will depend heavily on the type of process used and the implementation of the radio system. In an implementation in CMOS process where two radios are cooperating (a UWB radio and a narrowband radio), for example, the patch-ASIC chip can dissipate about 1 mW, 4 mW, or 10 mW of power and the base-ASIC chip can dissipate about 2 mW, 8 mW, or 20 mW of power.

The measurement of the amount of power dissipated or energy used is understood by those of ordinary skill in the art. It is understood that under normal operation, the ASIC chips are not using power at a constant level. As used herein, the power dissipation is generally measured while the radio is being used, that is, while the patch-ASIC chip and base-ASIC chip are in communication. The power numbers are generally mentioned for continual data transmission from the patch-ASIC chip to base-ASIC chip. The patch-ASIC chip power numbers include the power dissipation in the following circuits: capturing the data from the sensors, preprocessing of data to make it suitable for radio transmission, radio, and driving the antenna. The reverse order applies for the base-ASIC chip power. As used herein, the "continual data transmission" can be, for example, the patch-ASIC chip continually transmitting data from the sensors attached to it to the corresponding base-ASIC chip with the following conditions: (i) The source data rate of the sensor being of the order of 100 Kbits/sec, (ii) the wireless link reliability being very high in a typical indoor environment where healthcare systems are deployed (link reliability about 99.99%), and (iii) little to no loss of sensor data The continual transmission time can range from a few seconds to many days. For example, the transmission time can be about 2, 5 10, 30 or 60 seconds, or, 2, 5, 10, 30, or 60 minutes, or 2, 3, 6, 12, or 24 hours, or 2, 5, 10, 20, 30, 60 or 90 days.

In one aspect, the system includes a medical signal processor which communicates with a wireless distributed sensor system as its peripheral for detecting physiological parameters of the person and for providing signals indicative thereof. The term μ-Base as used herein is interchangeable with medical signal processor or MSP. In one embodiment, the medical signal processor wirelessly receives the signals from the distributed wireless sensor system in a multiplexed fashion and processes the signals to provide an indication of the health of the person. The indication of health could relate to a disease state, general health or fitness level of a person. In some embodiments, the system includes a mobile device for receiving the indication of the health of the person to allow for a diagnosis or treatment of the person, and a secure server for securely storing the at least one indication of health. The core processing resources of the medical signal processor, for example the μ-Base allows wireless distributed sensors to be ultra reliable/secure, ultra low power, ultra small and low cost. The peripheral wireless sensors can be a within a reasonable range of medical signal processor such as the base-ASIC chip. In some embodiments, the sensors are within 1 to 3 meters for example next to a bed in a hospital room. In some embodiments, the sensors are within 1 to 10 meters for example within a room. In some embodiments, the sensors are within 1 to 30 meters for example within a typical home.

A distributed sensor based mobile/remote monitoring system for the management of various types of diseases is disclosed. The system is capable of continuously monitoring a variety of parameters relating to the state of various diseases. The parameter monitoring can be continuous, periodic or episodic. The system is capable of continuous monitoring of given parameters from a few seconds to many days. A system to manage a particular type of disease or meet a health objective can be defined by selecting the appropriate parameters for that disease. For example, an ECG can be monitored on a patient in order to diagnose and prescribe treatments for cardiac care.

The present invention relates generally to health monitoring and more particularly to a health monitoring system that utilizes a medical signal processor or μ-Base with a wireless distributed sensor system. The following description is presented to enable one of ordinary skill in the art to make and use the invention and is provided in the context of a patent application and its requirements. Various modifications to the preferred embodiments and the generic principles and features described herein will be readily apparent to those skilled in the art. Thus, the present invention is not intended to be limited to the embodiments shown, but is to be accorded the widest scope consistent with the principles and features described herein.

To describe the feature of the medical signal processing system in more detail, refer now to the following description in conjunction with the accompanying figures.

FIG. 1A is an embodiment of a general architecture of a wireless medical signal processing system 100 in accordance with the present invention.

Figure 1B:
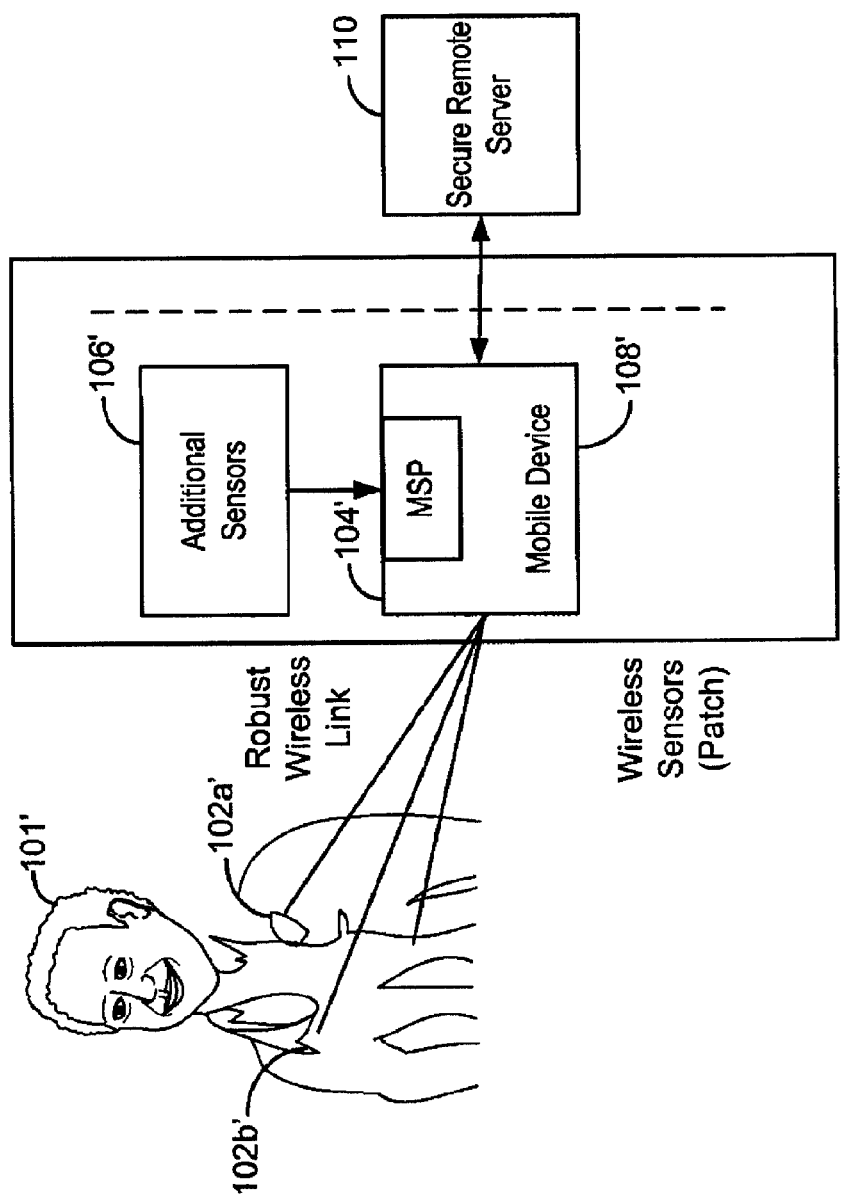
FIG. 1B is a block diagram of a second embodiment of a general architecture of a wireless health monitoring system in accordance with the present invention.

The system 100 is centered around a medical signal processor 104, such as a μ-Base that has a wireless distributed sensor network as its peripheral. The distributed sensor network includes a plurality of patches 102a-102n on a person 101. The patches 102a-102n can be internal to the body, coupled to the exterior of the body embedded in the garments or can be in close proximity of the body by some other means. In some embodiments, the patches comprise a μ-Patch and a patch-ASIC chip. The patches communicate wirelessly with MSP 104. In some embodiments, MSP 104 also includes its internal/local sensors 106, which can engage the body of the person, which are also part of the distributed sensor system. The medical signal processor (MSP) 104 in turn communicates with a mobile device 108. The mobile device 108 in turn communicates with a secure server 110 via a wireless or wired network. In this embodiment, the MSP 104 is a separate component from the mobile device 108. However, one of ordinary skill in the art readily recognizes that the MSP 104 could be incorporated into the mobile device as shown in FIG. 1B which is a second embodiment of the system 100. The MSP 104 also includes sensors 106, which can engage the body of the person, which are also part of the distributed sensor network. The MSP 104 has the ability to absorb significant processing burden from all of its distributed sensors to form a reliable wireless link with them. The MSP 104 also has the ability to communicate with all of its distributed sensors through a wireless uplink. It allows the MSP 104 to use its internal resources to monitor, control and dictate various performance factors of the distributed sensors to achieve the performance balance needed for any given application. The MSP 104 also can perform various house keeping functions for the overall medical signal processing system.

The mobile device 108 could be, for example, a cellular telephone, laptop, notebook, a smart phone, a PDA, a custom medical device or any stationary, portable, or mobile device which can communicate with the server over a network. Each component of the health monitoring system 100 will now be described in detail in conjunction with the accompanying figures.

Medical Signal Processing System

Figure 2:
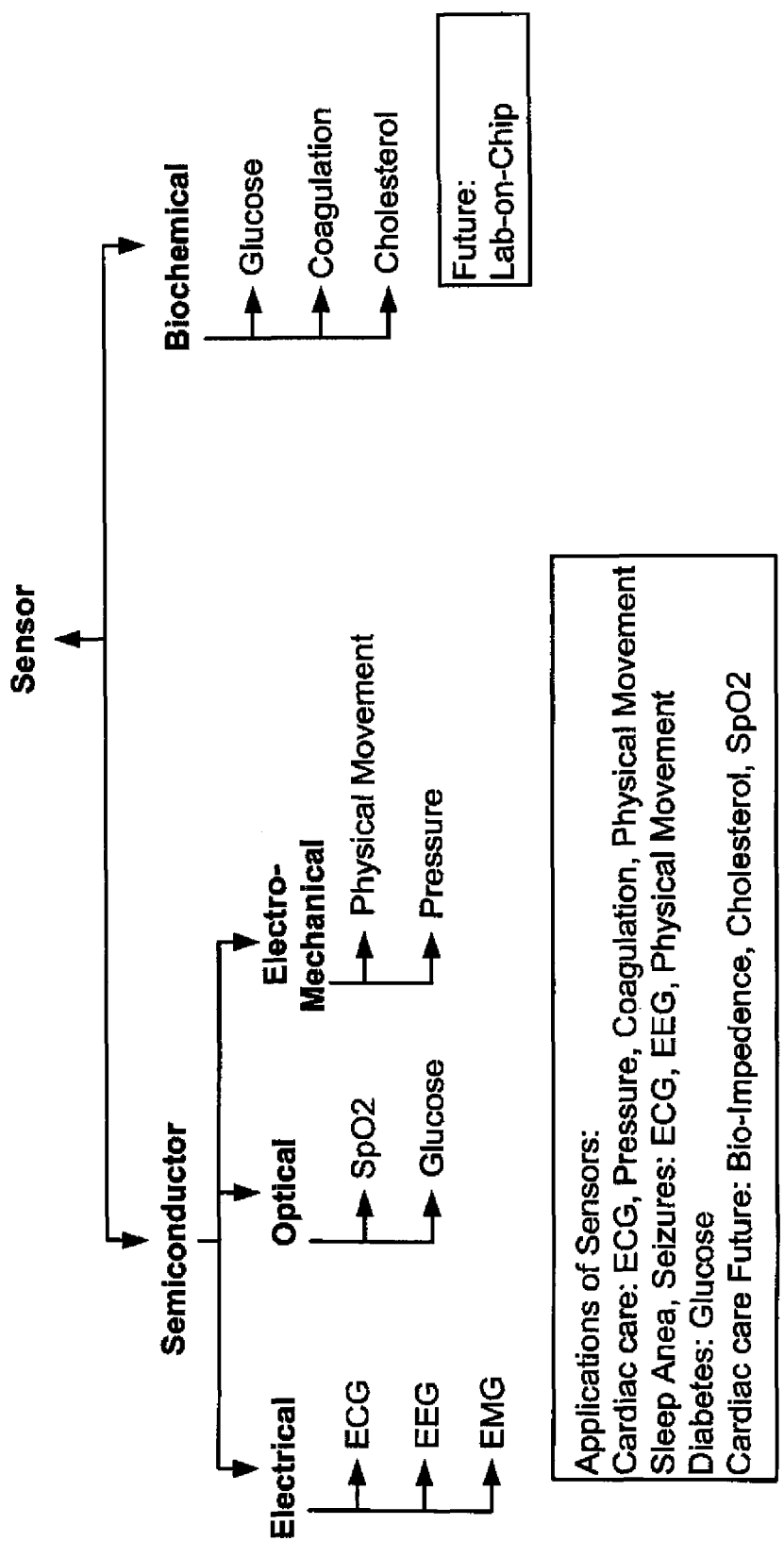
FIG. 2 illustrates examples of various sensors that can be included in a distributed sensor network.

As discussed above, the medical signal processing system as shown in FIGS. 1A and 1B can include a variety of sensors—either directly integrated in the medical signal processor or μ-Base 104, or linked to the medical signal processor 104 via a wireless link as patches 102 on the body of a user. Examples of various sensors that can be included in the distributed sensor system are shown in FIG. 2. Out of these examples, certain sensors can be chosen for implementation as patches 102, comprising, for example a patch-ASIC chip. Other sensors can be chosen for integration within the MSP 104. In this way, a variety of systems can be designed for the management of diseases, health and fitness, by choosing the sensors that monitor the appropriate parameters associated with target applications.

Modes of Operation: By using the distributed sensor network, the system of FIGS. 1A and 1B can monitor parameters in different ways. For example, by wearing patches on the body, the monitoring and/or transmission can be done continuously—e.g. continuously sensor data flowing from sensors in to the mobile device to the secure server. Patches can also be used for periodic or episodic monitoring. In some embodiments, the monitoring is done continuously, but the transmission is done in bursts. This is accomplished by using memory within the patch-ASIC chip to buffer data by storing the data for later transmission. In some embodiments, the data is stored in memory, and then regularly transmitted in bursts, for example, every second, every 10 seconds, every minute, every 2 minutes, every 5 minutes, every 10 minutes, or every 30 minutes. By transmitting in this regular burst mode, the patch can save energy over transmitting continuously because transmitting takes energy, and spending less time transmitting saves energy. The data transmitted in bursts is generally transmitted at a higher rate than the rate of sampling. In some embodiments, the data is stored in a buffer during a time period during which the patient wearing the patch is farther away from the μ-Base. This embodiment allows for energy to be conserved in the patch in the present invention due to the ability of the μ-Base to control the transmission mode of the patch. For example, the μ-Base can control the power at which the patch transmits data or the mode of transmission. The µ-Base can instruct the patch to store incoming data while the patch is farther away when it would take higher power and more energy to transmit, and later instruct the patch to send the data at lower power when the patch is closer to the µ-Base.

In some cases, the system is used in stand-alone mode. In a stand-alone mode, monitoring is normally done in an episodic or periodic mode by using the MSP 104 and sensors 106. For example, a cardiac rhythm can be directly monitored by pressing the MSP 104 against the body by using a built in ECG sensor. Another example of this stand-alone mode is glucose, cholesterol or blood coagulation monitoring. A drop of blood can be placed on a biochemical sensor that is built into the MSP 104 which can be converted to electrical signal by MSP for further processing. The glucose, cholesterol or blood coagulation rate reading will be registered in the sensor database on MSP 104 and/or mobile device 108 and/or the secure server 108.

Wearable Wireless Patches 102

Patches 102 are integrated circuit technology driven miniature wireless devices that can be conveniently attached to the body. Patches can also be designed for implanting within the body of a person. To achieve compactness, the patches 102 can be designed using a custom ASIC (a patch-ASIC chip) and a compact multi-chip module. The patches can be further simplified by leveraging the resources of MSP 104. The patch 102 in a preferred embodiment has two main parts: sensor circuits, and a radio core for the transmission of sensor data to other devices. In addition, it has a signal processor and power management circuits to achieve very low power dissipation. The sensor circuits can be directly incorporated in the custom ASIC and/or patch can also include a standalone sensor device whose data can be transmitted to other devices using the radio or ASIC on the patch. In a preferred embodiment, a person can wear a patch 102 for several days for continuous monitoring without changing or recharging the power source. Patches 102 can have the ability to receive wireless signals from the MSP 104 µ-Base to enhance its own power dissipation and improve its own wireless link reliability, based on the MSP's 104 monitoring of radio environment and application requirements. The patches 102 can also receive test/control signals from the MSP 104 to get authenticated and to check its own functionality.

Figure 3:
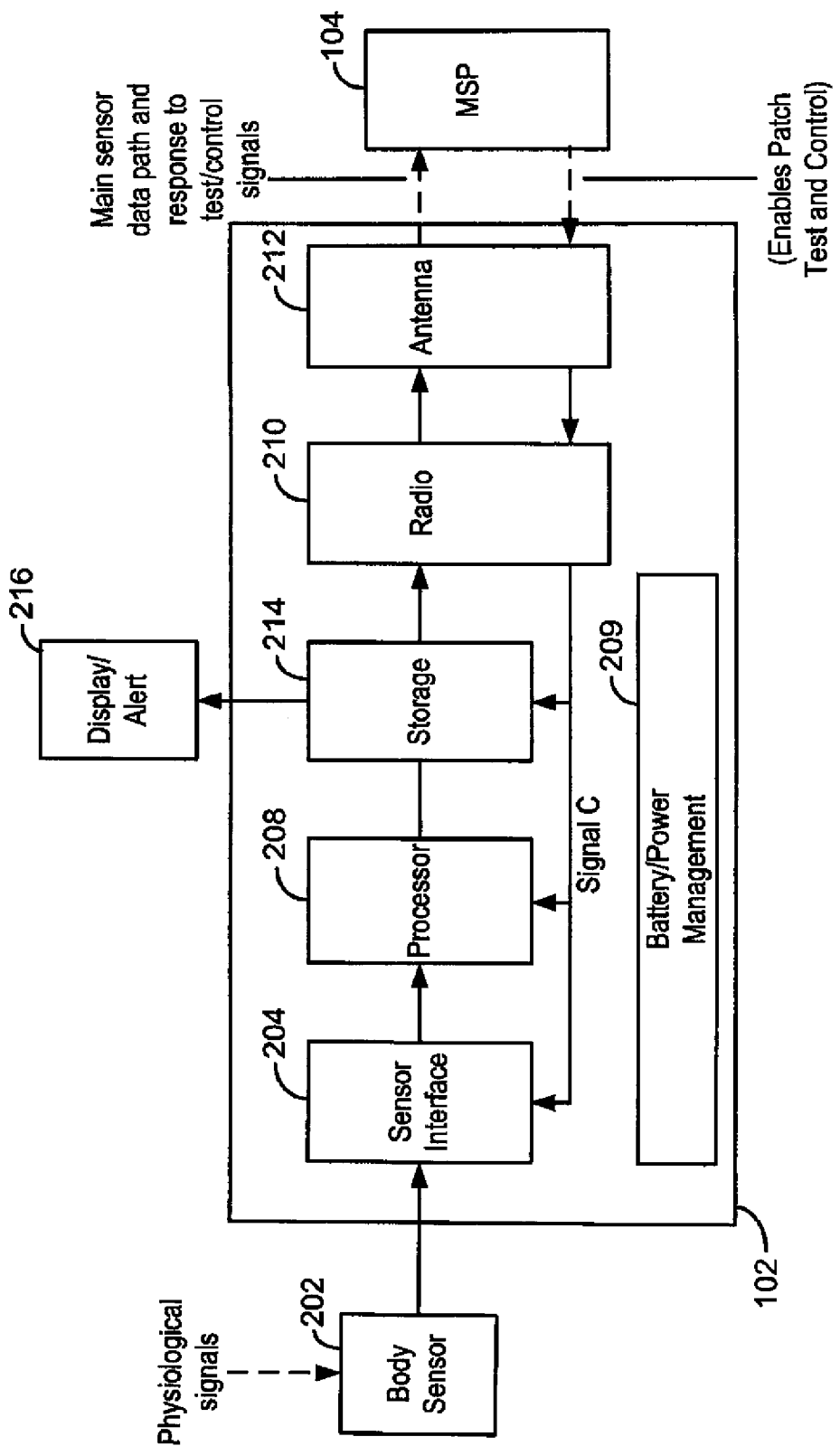
FIG. 3 illustrates a block diagram of a wireless patch in accordance with the present invention.

FIG. 3 illustrates a wireless patch 102 utilized in accordance with the present invention. The wireless patch 102 receives signals from a body sensor 202 via a sensor interface 204. The patch 102 may receive signals from a body it is either in contact with, or in close proximity of. The sensor interface 204 can receive electrical signals or other signals representative of different physiological parameters of the body. The output from the sensor interface 204 is provided to a processor 208 which processes the signal to perform various functions such as compression to reduce the data rate, encoding to achieve high reliability and manage buffering to vary duty cycle of radio. The processed data is presented to a storage element 214. The data from the storage element 214 is provided to a radio 210 which outputs the signal to a signal antenna 212. The storage element 214 can be adapted to be coupled to a local display/alert 216. A power source 209 provides power and power management to all elements of the patch 102. As shown, a wireless path through radio/antenna 210/212 also exists to receive test and control signals from the MSP 104 as discussed above. As shown, all resources of the patch 102 can be controlled by the MSP 104 by a signal C, wirelessly coming to patch 102 from the MSP 104.

Accordingly, by leveraging the information sent by MSP 104 via signal C, patches can dynamically alter the performance of their various functional blocks to choose trade off among high reliability, high security, low power and low cost for given applications of health monitoring.

Figure 3A:
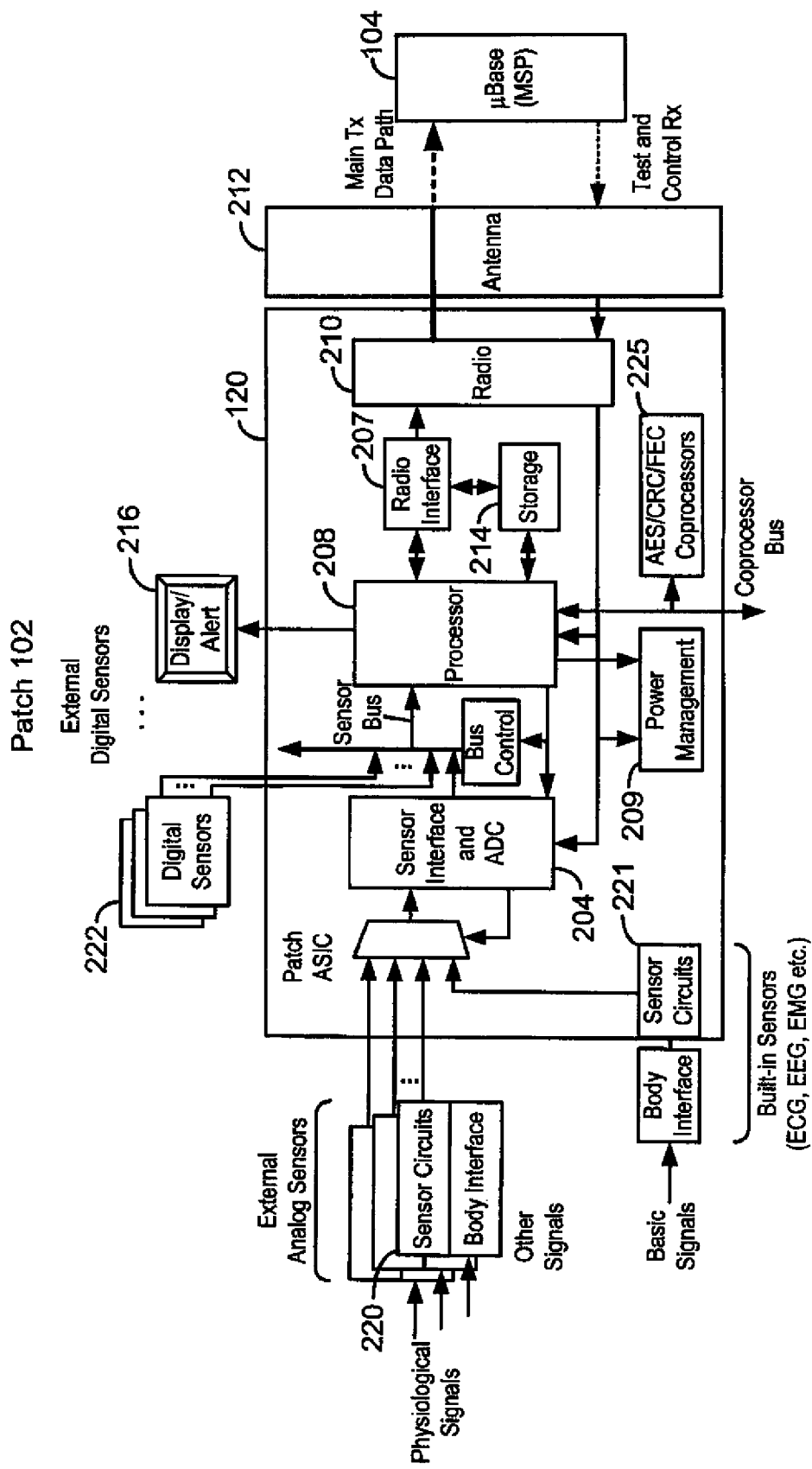
FIG. 3A illustrates a block diagram of another embodiment of a patch in accordance with the present invention.

FIG. 3A illustrates another embodiment of a wireless patch comprising a µ-Patch and a patch-ASIC. The wireless patch 102 comprises a patch-ASIC 120 which receives signals from either external analog sensors 220 or built in sensors 221 via a sensor interface 204 which has an analog to digital converter (ADC). The patch-ASIC 120 can also receive signals from digital sensors 222 that can that can be sent via the a sensor bus to the processor without passing through the sensor interface 204. The sensor interface 204 can receive electrical signals or other signals representative of different physiological parameters of the body. The output from the sensor interface 204 is provided to a processor 208 which processes the signal to perform various functions such as compression to reduce the data rate, encoding to achieve high reliability and manage buffering to vary duty cycle of radio. The processed data is presented to a storage element 214. The data from the storage element 214 is provided to a radio 210 via radio interface 207 which outputs the signal to a signal antenna 212. The processor 208 can be adapted to be coupled to a local display/alert 216. A power management circuit 209 connects to the processor 208 and exerts control over the elements of the patch to control the power that is supplied by a battery external to the µPatch. A wireless path through radio interface 207, radio 210 and antenna 212 also exists to send data to the µ-Base (MSP) 104 and to receive test and control signals from the µ-Base (MSP) 104 as discussed above. Here, the antenna 212 resides outside of the patch-ASIC 120 and is attached to a PCB on the µ-Patch along with the patch-ASIC. As shown, all resources of the patch 102 can be controlled by the MSP 104 by a signals received through the antenna. The patch-ASIC 120 can also have an encryption processor 225 having an AES, CRC, and/ or FEC coprocessors connected to the processor 208 for signal encoding and/or decoding. In some embodiments the encryption processor on the patch-ASIC has only circuits for encoding but not decoding circuits.

In summary, the trade off is possible due to any of or any combination of the following features:

a. A sensor interface to connect to a variety of physiological sensors b. A radio subsystem that can support a variety of communication schemes (e.g. different modulations including analog modulation, various codings, various data rates) to wirelessly communicate with a medical signal processor which is within a reasonable range, such as within a typical house c. A processor to support a variety of wireless communication schemes for radio system d. A processor that can implement various authentication and security schemes as desired by application e. Means to wirelessly receive a variety of test signals from a medical signal processor f. Means to run test signal though its data paths and generate output signals in response g. Means to wirelessly send resulting output signals back to medical signal processor h. Means to receive various control signals to reconfigure its various functional blocks i. Reconfigurable internal blocks to alter data rates, radio scheme, communication algorithm, power dissipation levels, etc.

j. sensors that can receive body's electrical physiological signals k. Encapsulation in a packaging material that can also provide a body interface l. Using its radio, generation of a RF beam that can be directed towards a part of person's body to probe internal parts m. Means to receive the RF signals scattered by body that can be analyzed to get information about the internals of the body n. Means to bring the device in a close proximity of body o. Means to attach the device to body p. Means to analyze and display the sensor data q. Means to alert a person as needed r. For ultra high reliability, ability of patches to wirelessly communicate with each other in case of loss of link by a patch to medical signal processor Medical Signal Processor (MSP) 104 (μ-Base)

The medical signal processor (MSP) 104 collects and receives data from the one or more of the distributed sensors (internal or external), and aggregates and processes this data. In addition, the MSP 104 can reliably transmit it to mobile device 100 in such a way that mobile device 100 in turn can transmit the data to a remote server system over wireless, cellular, or any type of wide area network (WAN).

The MSP 104 may have one or more of the following features:

1. to collect data from its internal/local sensors 2. radio/processors to receive data from external wireless sensors that are within a reasonable range, such as within a typical house 3. means to process and aggregate the sensor data based on an algorithm that can be programmed in MSP 104 to determine a diseases state and/or health state and/or fitness state 4. means to attach or connect or plug in to a mobile device 5. means to generate an alert based on the determination of the state of disease, health or fitness 6. means to locally display collected raw sensor data or processed data 7. means for transmission of collected raw sensor data or processed data to a remote server either directly or via a mobile device 8. means to enable continuous reliable transmission of sensor data over a cellular or wide area network 9. user interface to control the operation of monitoring system 10. means of a regular cell phone device (voice, data and image communication, display, keypad, etc.)

In addition to collecting and processing the data from all of its peripheral patches/sensors, the MSP 104 also has various means to wirelessly monitor and control all of its peripheral patches/sensors through a wireless uplink with them. Essentially, the MSP 104 becomes an integral part of the wireless medical signal processing system to achieve the overall requirements of the system—a major requirement being patches to be ultra reliable/secure, ultra low power, ultra small and low cost. The overall functionality of the system is asymmetrically partitioned between the patches 102 and MSP 104 to achieve these critical patch requirements.

Accordingly, MSP 104 may have the following features to achieve the system objectives:

1. means to act as a master of the overall system and patches/sensors to be its slaves 2. means to manage a distributed network of patches/sensors 3. means to authenticate, test and control the functionality of all of its peripheral patches/sensors 4. means to monitor/dictate the wireless link performance of its peripheral patches/sensors 5. means to monitor/dictate the power dissipation of its peripheral patches/sensors 6. means to dictate the degree of reliability of all of its peripheral sensors/patches 7. means to allow peripheral sensors/patches to use a very simple radio and have its own signal processor to complete the radio processing for patches/sensors 8. means to recreate the original sensor data if data has been compressed on the sensor/patches 9. means to monitor radio environment.

10. Radio to work with multiple communication schemes including digital and analog modulation The MSP (μ-Base) 104 can control the functionality and performance of its peripheral/patches based on the requirement defined for the overall system. The system performance can be dynamically adjusted, for example, due to a change in radio environment or a change in person's condition as monitored by the MSP 104.

Figure 4:
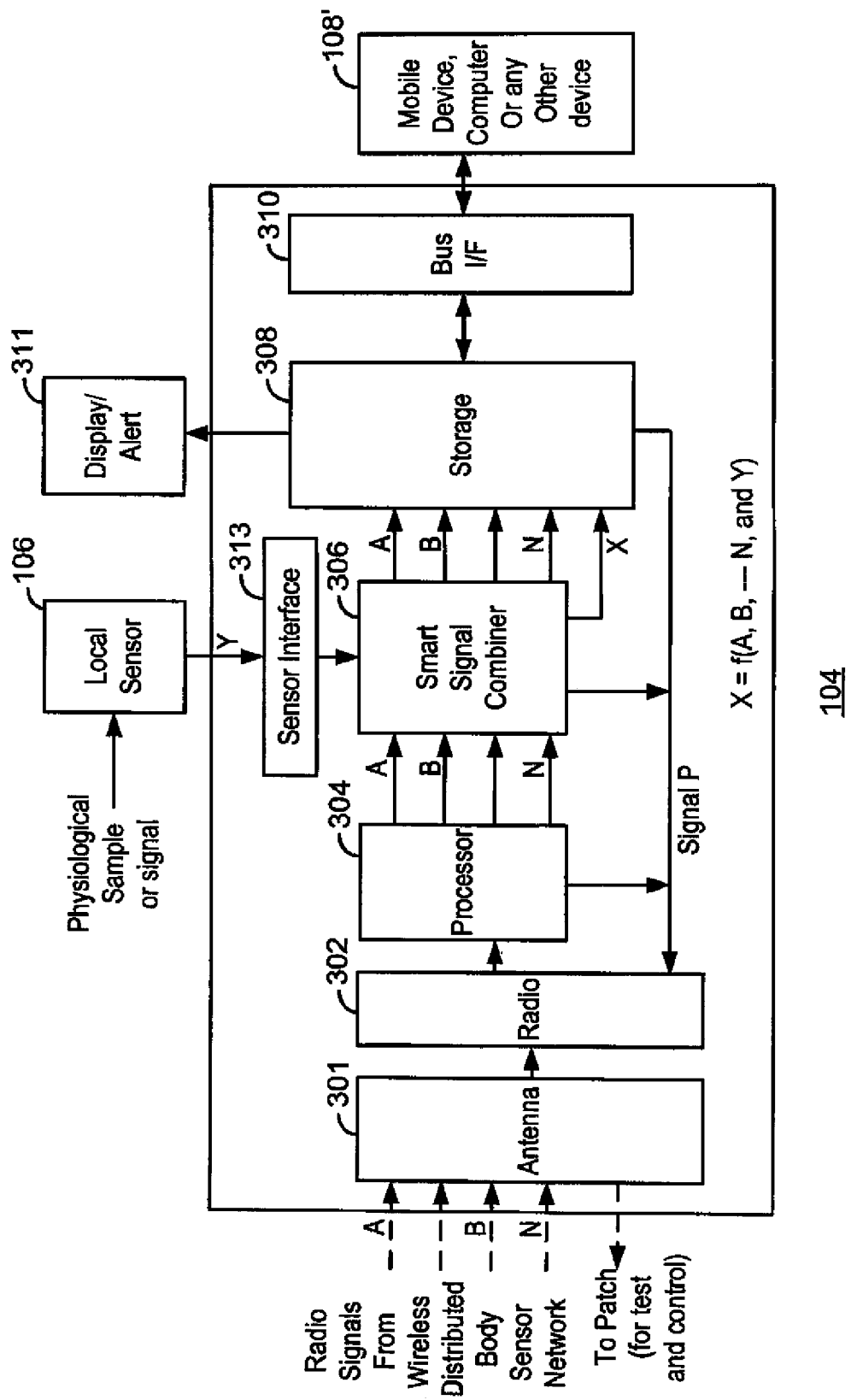
FIG. 4 illustrates a block diagram of a medical signal processor (µ-Base) in accordance with the present invention.

FIG. 4 illustrates an MSP (μ-Base) 104 in accordance with the present invention. An antenna 301 and a radio 302 within the MSP 104 receives a plurality of data signals (signals A-N) from the distributed sensor network. The radio 302 then provides these signals to a signal processor 304. The processor 304 then decodes the signals received by the radio 302. The decoded signals are then provided to a smart signal combiner 306, in a multiplexed or parallel fashion.

The smart signal combiner 306 includes a means for programming an algorithm for combining the signals to provide an indication of a state of the body. For example, certain sensor parameters taken together might indicate a disease state and/or heath state and/or fitness state of an individual.

The smart signal combiner 306 may also receive a signal Y from the local sensors 106 in the MSP 104. The signal Y represents either one signal from one local sensor or a plurality of signals from a plurality of local sensors. The smart signal combiner 306 also provides a signal (X) that is a parameter, relating to a state that has been measured utilizing a single sensor output or by combining the outputs of multiple sensors. This state is a result of one or several physiological parameters of the body and the signal X may be a function, computed over time, of one, all or a set of those sensor outputs (signals A-N) and sensor signals.

These various signals (A, B, . . . N, Y, X) are provided to a storage element 308 by the smart signal combiner 306. The storage element 308 may be any type of memory that can be utilized in integrated circuits. The storage element 308 can be adapted to be coupled to a local display/alert device 311 via the sensor interface 313. The data can then be retrieved by the mobile device from the storage element 308 via a bus interface 310. As before mentioned, the MSP 104 can either be part of the mobile device 108 or a stand alone device.

All these resources enable MSP 104 to act as a stand-alone device to provide the needed information locally to concerned parties or it can transmit the information to a remote secure server for further processing and access. The information can be used locally, or remotely, to diagnose/treat a disease or for general health/fitness management of a person. As shown, MSP 104 also has a wireless path to communicate with patches/sensors to monitor and control their performance. In a control mode, radio 302 operates in an uplink mode by sending test/control data via signal P over the wireless link. This control mode is activated when the MSP 104 needs to test, monitor and/or control its peripheral patches/sensors via the processor 304. The processor 304 should be for example, a microprocessor with signal processing capability that executes the various functions.

The processor 304 can utilize other resources such as smart signal processor 306 and storage 308 to carry out its control/test related and general processing tasks. In the control mode, for example, the processor 304 can generate test signals and send to a patch 102, and analyze the signals received from the patch 102 to estimate its wireless link performance. If needed, the MSP 104 can then send control signals to alter the wireless link performance by changing certain parameters relating to radio functions of the patch 102, for example by instructing signal processor 208 and radio 210. In some implementations, some of the internal blocks of MSP 104, such as processor 304, smart signal processor 306 and storage 308 can be implemented in software. This implementation is likely when MSP 104 functionality is embodied within a mobile device, computer, a custom medical device, or any other device.

Figure 4A:
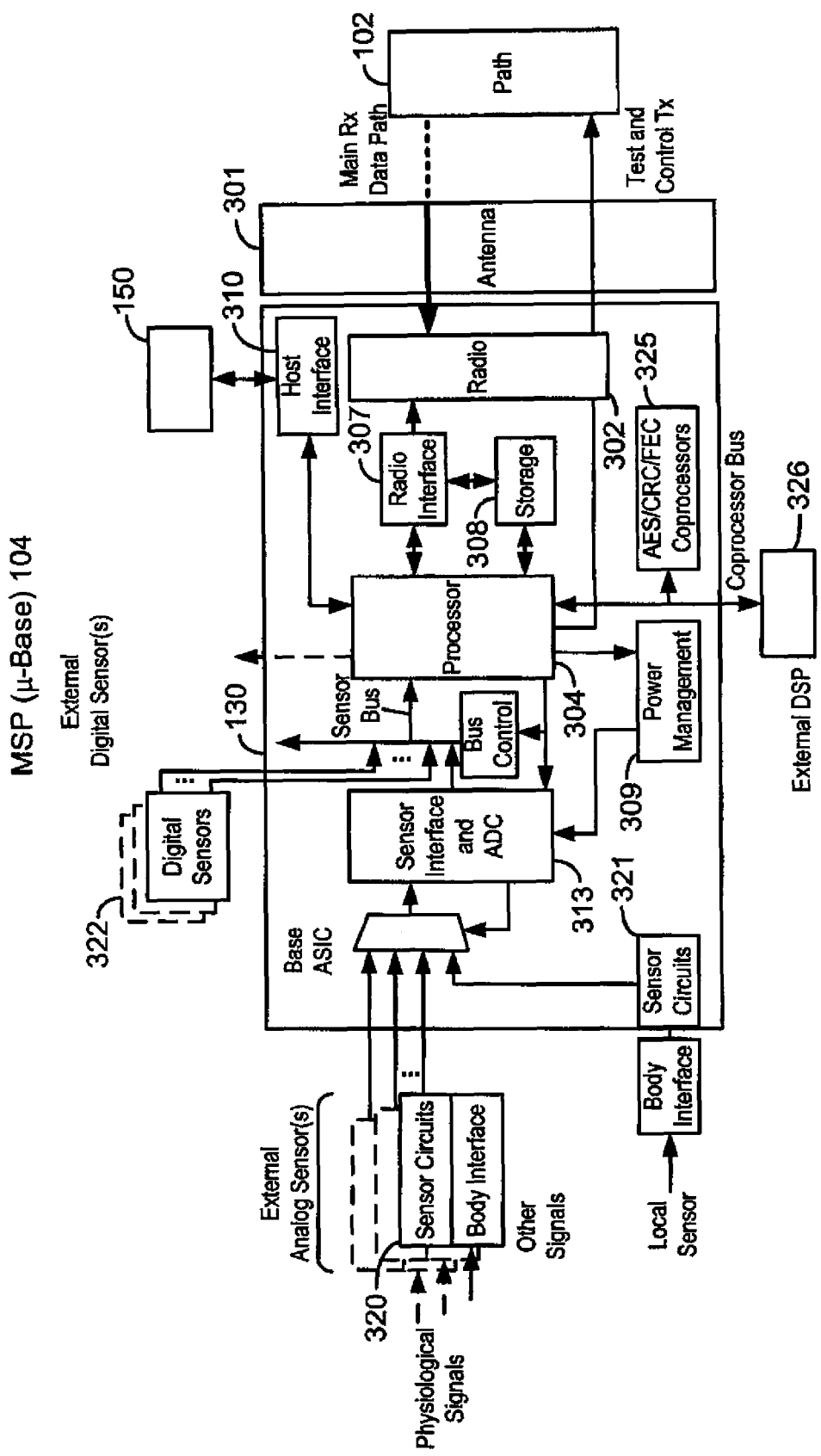
FIG. 4A illustrates a block diagram of another embodiment of a medical signal processor (µ-Base) in accordance with the present invention.

FIG. 4A illustrates another embodiment of an MSP (μ-Base) 104 of the present invention. The μ-Base 104 comprises a base-ASIC 130. An antenna 301 is connected to the base-ASIC 130 through a PCB to which the base-ASIC 130 and antenna 301 are also attached. The antenna sends signals to the radio 302 that it receives data from the patch 102. The radio 302 then provides these signals to a signal processor 304 through radio interface 307. The processor 304 then decodes and can further process the signals received by the radio 302. The processor can send the data to storage element 308. The data can then be retrieved from storage element 308 and sent to a host device 150 (which could, for example, be a mobile device 108) through the host interface 310. As shown, MSP 104 also has a wireless path to transmit to with patches/sensors to monitor and control their performance. In a control mode, radio 302 operates in an uplink mode by sending test/control data over the wireless link. This control mode is activated for the MSP 104 to test, monitor and/or control its peripheral patches/sensors/gates via the processor 304. The processor 304 should be for example, a microprocessor with signal processing capability that executes the various functions. In the control mode, for example, the processor 304 can generate test signals and send to a patch 102, and analyze the signals received from the patch 102 to estimate its wireless link performance. If needed, the MSP 104 can then send control signals to alter the wireless link performance by changing certain parameters relating to radio functions of the patch 102, for example by instructing signal processor 208 and radio 210. The base-ASIC 130 also has the capability of receiving signals from external analog sensors 320 or local analog sensors 321 to the processor 304 through sensor interface 313. The base-ASIC can also receive signals from digital external sensors 322 to the processor 304. The base-ASIC 130 can also have an encryption processor 325 having for example AES. CRC, and/or FEC coprocessors connected to the processor 208 for signal encoding and/or decoding. In addition, as shown, the processor 304 is connected to a digital signal processing chip (DSP) 326 through a coprocessor bus for performing smart antenna protocols such as beam-forming or for processor intensive decoding algorithms. A power management circuit 309 connects to the processor 304 and exerts control over the elements of the patch to control the power that is supplied by a power supply external to the MSP.

The functionality of MSP 104 allows its distributed sensors (patches) to maintain high wireless reliability, high security, low power and low cost. Furthermore, the versatility of MSP 104 allows it to create a variety of different types of medical systems. To allow this functionality and versatility, in summary, it can include any of or any combination of the following features:

a. Means to wirelessly communicate with a plurality of peripheral wireless physiological sensors in a multiplexed fashion that are within a reasonable range, such as within a typical house b. Means to manage a network of plurality of said sensors as their master c. Means to display health state information or the data received from peripheral sensors d. Means to alert a person about health state e. Means to connect to a mobile device to exchange information with it and to communicate with a remote server through mobile devices connectivity to a wide area network f. Partitioning of its functions between hardware and software to allow its integration within a mobile device g. Means to wirelessly send a variety of test signals to its peripheral sensors and analyze the received signals to monitor the proper functioning of the sensors and their various internal functional blocks h. Means to send various control signals to peripheral sensors to configure their various functional blocks:

i. Means to monitor peripheral sensors to determine their respective power dissipation rates and the state of their power sources; to supervise power management j. Means to monitor surrounding radio environment to determine an optimum wireless communication scheme at any given instance k. Means to instruct peripheral sensors to utilize a particular radio/communication mode for reliable operation l. Means to authenticate peripheral sensors m. Means to monitor various security aspects of peripheral sensors n. Means to allow coupling to local sensors through a wired connection o. A processor to support the execution of a variety of communication algorithms/schemes to allow peripheral sensor to use the simplest possible communication scheme for a given application to minimize sensors power and resource requirements by absorbing the burden of processing (asymmetric communication scheme)

p. A smart signal combiner that can be programmed to run needed algorithms to (i) analyze signals from one or more peripheral sensors over time, and/or (ii) combine signals from a plurality of peripheral sensors; to determine a health state q. Storage media to store the health state information and/or raw data received from peripheral sensors Mobile Device 108

The mobile device 108 could be, for example, a cellular telephone, laptop, notebook, a smart phone, a PDA, a custom medical device or any mobile device which can communicate with the server over a wide area network and/or Internet. The mobile device 108 can also be a regular cell phone handset, which has been modified to include the appropriate features and means to work with MSP 104. The mobile device 108 communicates with the MSP 104. In one embodiment, the MSP can be built within mobile device 108 as part of the mobile device design. In this mode, many internal functions of MSP can be implemented in software. In most cases, MSP's radio system and sensor interfaces will remain intact in hardware.

Secure Server 110

The secure server 110 receives data from distributed sensors over a cellular telephony network, any type of wide area network or Internet via MSP 104 and the mobile device 108. The server 110 further processes the received data from the mobile device and stores it in a secure location. The server 110 may also contain various types of software programs, including software to manage health information databases (such as electronic medical records, computerized purchase orders and computerized prescription systems). The secure server 110 may also have the middleware to process/link sensor data to such health information databases.

The data stored on the secure server 110 may be accessed by a healthcare provider, caregiver or patient via the Internet by using any type of terminal device such as computer, mobile device, cell phone, smart phone or personal data assistant (PDA).

The health monitoring system in accordance with the present invention supports many classes of sensors for physiological data collection, such as:

1. The health monitoring system supports many classes of sensors for physiological data collection, such as:
   a. Sensors (either patches 102 or sensors 106) contacting the body 101 through gels, etc.
   b. Patches 102 embedded within the body 101 through surgical procedures.
   c. Patches 102 probing the body 101 through micro-needle based skin punctures.
   d. Sensors in close proximity of the body 101—e.g., probing using a microwave or optical beam.
   e. Sensors embedded in the MSP 104 or mobile device 108 for periodic or occasional use.
   f. Sensors that can read biochemical micro-fluidic test strips (e.g. glucose, blood coagulation rate) via electrical or optical sensor
2. The health monitoring system in accordance with the present invention can support one of these sensors and/or patches or multiple sensors and/or patches from multiple classes.
3. The MSP 104 has the ability to collect data in real time from many such sensors and/or patches and to apply a chosen algorithm to combine signals from various sensors and/or patches to determine or predict a physiological or disease state.
4. The MSP 104 can store data for local use and/or transmit in real time to a remote server for use by clinicians and other parties. If desired, some of the MSP 104 functions can be implemented on a remote sensor.
5. As stated above, one function of the MSP 104 is physiological data processing.
6. The second function of MSP 104 is to manage all patches and/or sensors for optimal functionality—managing authentication/security functions, monitor and enhance the radio transmission performance of patches and/or sensors to increase link reliability, monitor and minimize power dissipation by patches and/or sensors.

The health monitoring system in accordance with the present invention can be utilized in a variety of environments. One example is the cardiac disease management system. To describe the features of such a system refer now to the following description in conjunction with the accompanying figures.

A Mobile/Remote Monitoring System for Cardiac Disease Management

Figure 5:
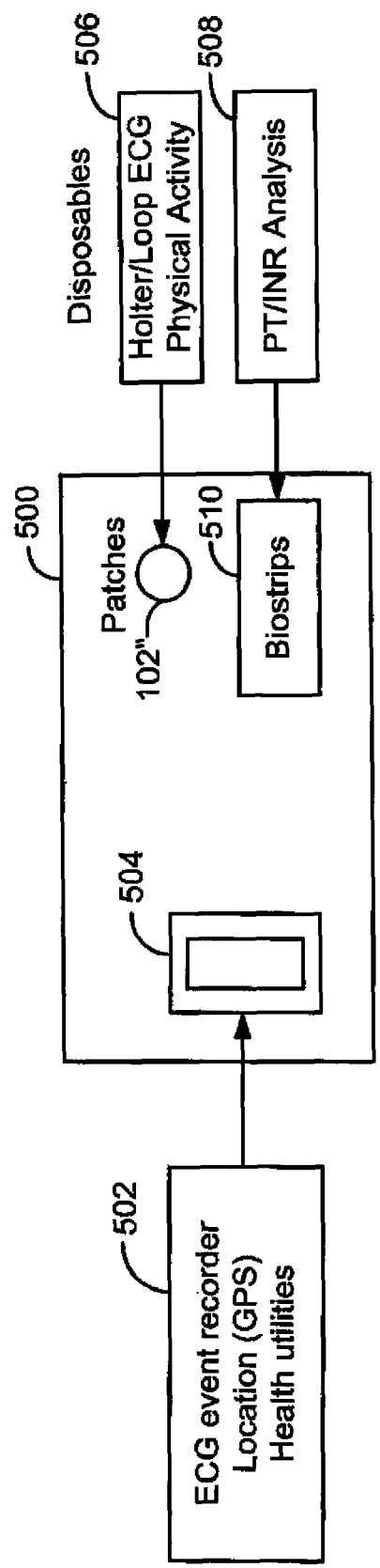
FIG. 5 is a block diagram of a cardiac care product in accordance with the present invention.

An embodiment of a cardiac disease care product in accordance with the present invention is described herein below. FIG. 5 is a block diagram of a cardiac care product in accordance with the present invention. The cardiac care product includes a mobile device 504 which utilizes patches 102" and biostrips as sensors 510. The mobile device 504 includes an ECG event recorder 502, a geographic positioning system (GPS) and health utilities. The patches may include a Holter mechanism and a loop ECG monitor 506 as well as accelerometers for detecting physical activity. The biostrips 510, which are basically microfluidic test strips, may be utilized, for example, for anticoagulation analysis of the blood (PT/INR).

Figure 6:
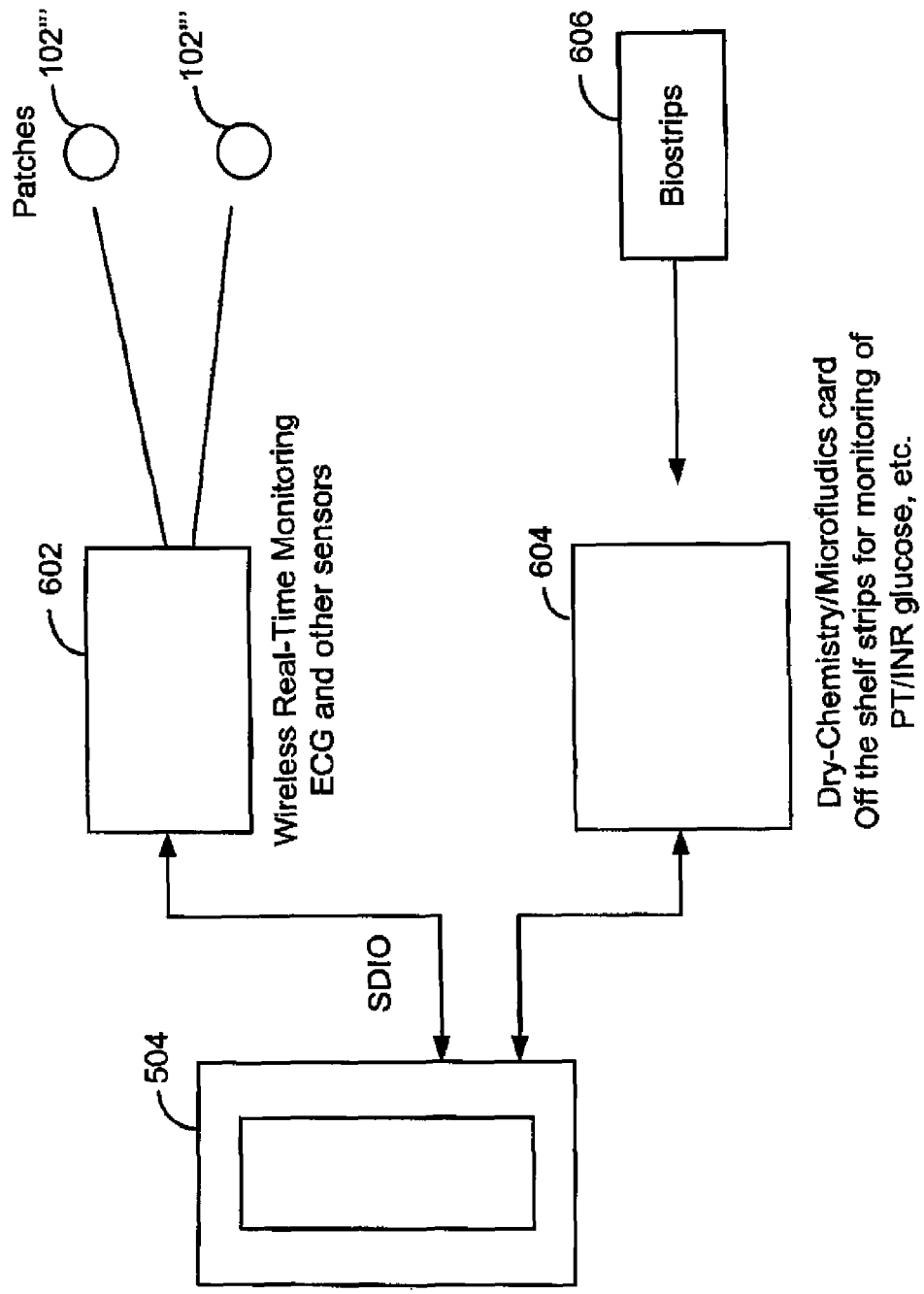
FIG. 6 is a block diagram of an implementation of a mobile device utilized with the cardiac care product of FIG. 5.

FIG. 6 is a block diagram of one implementation of a mobile device utilized with the cardiac care product of FIG. 5. The mobile device 504 may receive a first SD (Secure Digital) card 602 that includes wireless real-time monitoring system. The SD card 602 receives data from patches 102"" and other sensors. The mobile device 504 also may receive a second SD card 604 that monitors PT/INR, glucose and the like. The second SD card receives its data via biostrips 606 that can be activated by a drop of patient's blood, for example. The PT/INR and/or glucose reading is obtained by building an electrical or optical reader on the second SD card that can read the biostrips. The cardiac care product can be used for the management of various cardiac diseases, including arrhythmia. In an embodiment, this cardiac care product monitors the following parameters:

1. ECG signals (time duration programmable—few seconds to few weeks)
2. Pulse and respiration
3. Patient's physical movement
4. Blood coagulation analysis for drug therapy for the treatment of arrhythmia
5. A mobile, integrated system for remote cardiac care is provided—It is a system that is useful for diagnosis and treatment of various cardiac diseases.
6. Its core functions are listed below:
   a. Wireless AECG—duration programmable from a few seconds to 30 days to serve a variety of functions including Holter monitoring, cardiac event monitoring, cardiac loop monitoring (wireless ECG sensor patches and receiver)
   b. PT/NR based blood anticoagulation analysis (dry chemistry microfluidic strip and optical/electrical reader/sensor)
7. Its auxiliary functions are listed below:
   a. Patient activity recording (accelerometer sensor)
   b. Patient location information (GPS)
   c. Ability to connect to an implanted wireless pacemaker
   d. Medication schedules (software)
   e. Doctor visit and treatment schedule (software)
8. Microfluidic biostrip/reader concept can also be used for glucose monitoring
9. The system can be built by integrating the electronics inside a mobile device/computer or an attachment to a mobile device/computer. The mobile device 504 may or may not be connected to a remote server through a network.

The sensors for parameter monitoring may be distributed between the patches 102"" and the mobile device 504 as follows:

Patches 102

The patches 102"" have sensors to continuously monitor ECG, pulse, respiration and patient's physical movement. ECG function can be programmed to work in any mode as prescribed by a physician, such as:

a. Continuous ECG: for any amount of time (e.g. 24 Hrs, 48 Hrs, seven days, thirty days).

b. ECG Loop recorder: Shorter time recordings with continuous overwriting

Patient's physical movement data is recorded along with ECG data on a continuous basis. In addition, pulse and respiration are recorded as desired.

MSP 104

In a stand-alone mode, the mobile device 504 has the means to monitor a few different parameters as below:

a. ECG Event Recording: Via built-in ECG sensor, mobile device 504 is able to record ECG signals for any duration as desired. In this mode, the mobile device 504 is directly held to the body 101.

b. Biochemical parameters: The mobile device 504 has a built in biochemical sensor, electrical sensor and an optical sensor. Any of these sensors can be used to read certain parameters relating to disease management. For example, the MSP 104 can register blood coagulation readings for PT/INR (Prothrombin Time/International Test Ratio) analysis for Warfarin drug therapy. For this application, a test strip with a blood drop mixed with a chemical reagent can be inserted into the MSP 104 to determine blood anticoagulation rate for PT/INR analysis.

A distributed sensor based mobile/remote monitoring system for the management of various types of diseases is disclosed. The system is capable of continuously monitoring a variety of parameters relating to the state of various diseases. The parameter monitoring can be continuous, periodic or episodic. Some of the parameters that can be monitored by the system are ECG (electrocardiograph), EEG (electroencephalograph), EMG (Electromyography), blood glucose, pulse, respiration, blood pressure, temperature, $SpO_2$, body fluid density, blood density, patient physical movement and patient physical location. A system to manage a particular type of disease can be defined by selecting the appropriate parameters for that disease. The system can be applied to manage many type of diseases and conditions, such as—arrhythmia, heart failure, coronary heart disease, diabetes, sleep apnea, seizures, asthma, COPD (Chronic Obstructive Pulmonary Disease), pregnancy complications, wound state, etc.

An innovative technology base is needed to address wide ranging applications and to meet critical requirements for the mass market—high reliability, high security, low power, small form factor and low cost. The technology disclosed meets this goal. The technology involves a medical signal processor (MSP) closely supervising all aspects of functionality of its peripheral wireless patches to help achieve the objectives. The patches are simple while the medical signal processor (MSP) has all the smarts to work with patches. It results in asymmetric processing load on MSP and patches—patches are simple and reconfigurable and MSP has the complexity to take the processing burden from them for wireless communication link, and processing load to supervise patches. Both the MSP and the patches have various resources to build complete self contained systems to determine a health state of a person from sensor physiological data and to display and/or send data to another device for further processing.

One aspect of the invention is a method for monitoring a physiological condition using two or more ASIC chips and a host device wherein the chips are designed to work together to measure physiological signals, wherein (a) one of the chips is a patch-ASIC chip incorporated into a physiological monitoring patch comprising a sensor interface for measuring physiological signals, a processor for processing the signals into sensor data, memory for storing data relating to the signals, a radio for transmitting sensor data, and power management circuits for controlling power on the chip; and (b) one of the chips is a base-ASIC chip comprising a processor for processing sensor data, memory for storing data relating to the signals, a radio for transmitting instructions to the patch-ASIC chip, power management circuits for controlling power on the chip, and a host interface allowing the base-ASIC chip to communicate with the host device; wherein the base-ASIC chip controls a function of the physiological signal monitoring patch.

Some embodiments of the method are methods to manage a patient's disease. They types of diseases that can be managed include arrhythmia, heart failure, coronary heart disease, diabetes, sleep apnea, seizures, asthma, COPD, pregnancy complications, and wound state.

Some embodiments of the method are methods to manage a condition related to the wellness and fitness of a person. The types of conditions that can be managed include weight loss, obesity, heart rate, cardiac performance, dehydration rate, blood glucose, physical activity or calorie intake, or combinations thereof.

One aspect of the invention is method for unsupervised placement of a physiological patch that involves: (a) placing the patch that can receive wireless signals from a base device wherein the patch comprises a visual marker to help the user orient the patch on the patient's body; (b) initializing the patch with a base device by automatic verification of proper placement of the patch; and (c) indicating the proper or improper placement of the patch to the user with an audio or visual indication. The indication of proper placement can be provided by an audio or visual signal either on the patch, on the base device, on the host device, or on another device.

One aspect of the invention is a business method relating to the production and use of sets of ASIC chips that are designed to work together to measure physiological signals. The business method involves manufacturing both a patch-ASIC chip and a base-ASIC chip that are designed to work together to wirelessly communicate physiological data, wherein each chip each comprises a processor, memory storage, a radio, and circuits for power management. In some embodiments, the chips are designed to be used with a plurality sensor types. The method comprises selling and/or licensing the patch-ASIC chip and base-ASIC chip to multiple customers for incorporation into physiological sensing systems. This business model contemplates the value of selling a chip set that can be used in multiple types of physiological monitoring applications. The fact that the chips are designed to work together to conserve energy and to maximize communication provides value to the system manufacturer and the end user. The fact that the chips can be used in multiple applications allows the volume of ASIC chip manufacturing to be high enough to provide to provide the economy of scale to make the ASIC devices cost effective. The plurality of sensor types include sensors that measure ECG, EEG, EMG, $SpO_2$, tissue impedance, heart rate, and accelerometer signals.

The business methods can be applied to sensor systems for monitoring a patient disease or for monitoring health and fitness conditions as described above.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for measuring physiological signals, comprising:
 (a) a patch-ASIC chip adapted for incorporation into a physiological signal monitoring patch comprising a sensor interface, a processor coupled to the sensor interface, a memory element coupled to the processor, a radio comprising an ultra wideband (UWB) transmitter and a narrowband receiver coupled to the memory element that transmits sensor data via the UWB transmitter to a base-ASIC chip and/or a gate-ASIC chip and receives instructions from the base-ASIC chip and/or gate-ASIC chip via the narrowband receiver, and power management circuits that coordinate power on the patch-ASIC chip;
(b) the gate-ASIC chip comprising a processor that processes sensor data, a memory element coupled to the processor, a radio transceiver coupled to the processor that directs communication between the patch-ASIC chip and the base-ASIC chip, and power management circuits that coordinate power on the gate-ASIC chip; and
(c) the base-ASIC chip comprising a processor that processes sensor data, a memory element coupled to the processor, a radio comprising a UWB receiver and a narrowband transmitter coupled to the memory element that transmits said instructions to the patch-ASIC chip and/or the gate-ASIC chip via the narrowband transmitter and receives said sensor data from said patch-ASIC chip and/or said gate-ASIC chip via the UWB receiver, power management circuits that coordinate power on the base-ASIC chip, and a host interface through which the base-ASIC chip communicates with a host device,
wherein the base-ASIC chip is programmed to use more processing resources than the patch-ASIC chip.

2. The system of claim 1 wherein the base-ASIC chip is incorporated into a Base, the patch-ASIC chip is incorporated into a μ-Patch, and the gate-ASIC chip is incorporated into a μ-Gate; wherein each of the μ-Base, μ-Patch, and μ-Gate comprise a printed circuit board and an antenna attached to the printed circuit board for transmitting radio signals.

3. The system of claim 2 wherein the base-ASIC chip can switch the transmission mode of the μ-Patch and/or the μ-Gate between UWB and narrowband radio.

4. The system of claim 1, wherein the patch-ASIC chip is configured to wirelessly transmit data to the base-ASIC chip and/or gate-ASIC chip for at least about 2 days while measuring a physiological signal from a subject without changing or recharging a battery coupled to the patch-ASIC chip.

5. The system of claim 1, wherein the base-ASIC chip and the patch-ASIC chip are programmed such that the ratio of power dissipation of the base-ASIC chip to power dissipation of the patch-ASIC chip is at least about 3:2.

6. A method for monitoring a physiological condition, comprising:
(a) receiving signals from a sensor at a patch-ASIC chip that is incorporated into a physiological signal monitoring patch, the patch-ASIC chip comprising a sensor interface coupled to the sensor, a processor coupled to the sensor interface, a memory element coupled to the processor, a radio comprising an ultra wideband (UWB) transmitter and a narrowband receiver coupled to the memory element;
(b) managing the power dissipation on the patch-ASIC chip with power management circuits on the patch-ASIC chip;
(c) transmitting, via the UWB transmitter of the patch-ASIC chip, data signals to a base-ASIC chip, wherein said data signals are transmitted through an antenna incorporated into the patch;
(d) receiving, via a UWB receiver of said base-ASIC chip, the data signals at said base-ASIC chip, said base-ASIC chip comprising a processor that processes data signals, a memory element coupled to the processor, a radio comprising said UWB receiver and a narrowband transmitter coupled to the memory element, power management circuits that coordinate power dissipation on the base-ASIC chip, and a host interface through which the base-ASIC chip communicates with a host device; and
(e) sending, via said narrowband transmitter of said base-ASIC chip, instructions wirelessly from the base-ASIC chip to the patch-ASIC chip such that the base-ASIC chip coordinates a function of the physiological signal monitoring patch;
(f) receiving, via said narrowband receiver of said patch-ASIC chip, said instructions sent in (e); and
(g) keeping track, using the base-ASIC chip, of the quality of the wireless links between ASIC chips, and sending commands to the patch-ASIC chip and/or gate-ASIC chips to instruct the chips to switch between UWB and narrowband radio or to raise or lower transmit power in order to lower power consumption or to enhance communication quality,
wherein the base-ASIC chip uses more processing resources than the patch-ASIC chip.

7. The method of claim 6 further comprising coordinating, by the base-ASIC chip, one or more of the following functions: initialization and link set up, power management, data packet routing, type of transmission radio, radio transmit-power, radio receive-sensitivity, patch operational integrity, audio signal generation, display activation, or a combination thereof.

8. The method of claim 6 further comprising utilizing a packet-data protocol for the ASIC chips and coordinating data packet routing using the base-ASIC chip.

9. The method of claim 6, wherein the patch-ASIC chip is configured to wirelessly transmit data to the base-ASIC chip and/or gate-ASIC chip for at least about 2 days while measuring a physiological signal from a subject without changing or recharging a battery coupled to the patch-ASIC chip.

10. The method of claim 6, wherein the base-ASIC chip consumes at least about 50% more power than the patch-ASIC chip.

11. A method for monitoring a physiological condition, comprising:
receiving signals from a sensor at a patch-ASIC chip that is incorporated into a physiological signal monitoring patch, the patch-ASIC chip comprising a sensor interface coupled to the sensor, a processor coupled to the sensor interface, a memory element coupled to the processor, a radio comprising an ultra wideband (UWB) transmitter and a narrowband receiver coupled to the memory element;
managing the power dissipation on the patch-ASIC chip with power management circuits on the patch-ASIC chip;
transmitting, via the UWB transmitter of the patch-ASIC chip, data signals to a base-ASIC chip, wherein said data signals are transmitted through an antenna incorporated into the patch;
receiving, via a UWB receiver of said base-ASIC chip, the data signals at said base-ASIC chip, said base-ASIC chip comprising a processor that processes data signals, a memory element coupled to the processor, a radio comprising said UWB receiver and a narrowband transmitter coupled to the memory element, power management circuits that coordinate power dissipation on the base-ASIC chip, and a host interface through which the base-ASIC chip communicates with a host device; and
sending, via said narrowband transmitter of said base-ASIC chip, instructions wirelessly from the base-ASIC chip to the patch-ASIC chip such that the base-ASIC chip coordinates a function of the physiological signal monitoring patch;
receiving, via said narrowband receiver of said patch-ASIC chip, said sent instructions; and authenticating the patch-ASIC chip by bringing the physiological signal monitoring patch in proximity of the device comprising the base-ASIC chip,
wherein the base-ASIC chip uses more processing resources than the patch-ASIC chip.

12. The system of claim 11 further comprising wirelessly exchanging, using the base-ASIC chip, shared keys with the patch.

13. The method of claim 11 further comprising coordinating, by the base-ASIC chip, one or more of the following functions: initialization and link set up, power management, data packet routing, type of transmission radio, radio transmit-power, radio receive-sensitivity, patch operational integrity, audio signal generation, display activation, or a combination thereof.

14. The method of claim 11 further comprising utilizing a packet-data protocol for the ASIC chips and coordinating data packet routing using the base-ASIC chip.

15. The method of claim 11 wherein the patch-ASIC chip is configured to wirelessly transmit data to the base-ASIC chip and/or gate-ASIC chip for at least about 2 days while measuring a physiological signal from a subject without changing or recharging a battery coupled to the patch-ASIC chip.

16. The method of claim 11 wherein the base-ASIC chip consumes at least 50% more power than the patch-ASIC chip.

17. A method for monitoring a physiological condition, comprising:
(a) receiving physiological signals from one or more sensors at a patch-ASIC chip incorporated into a physiological signal monitoring patch, the patch-ASIC chip comprising a sensor interface, a processor coupled to the sensor interface, a memory element coupled to the processor, a radio comprising an ultra wideband (UWB) transmitter and a narrowband receiver coupled to the memory element that transmits data via the UWB transmitter to a base-ASIC chip and/or a gate-ASIC chip and receives instructions from the base-ASIC chip and/or gate-ASIC chip via the narrowband receiver;
(b) managing power dissipation on the patch-ASIC chip with power management circuits on the patch-ASIC chip;
(c) transmitting data from said UWB transmitter of the patch-ASIC chip to said gate-ASIC chip through an antenna in the patch;
(d) receiving at the gate-ASIC chip said data transmitted in (c), the gate-ASIC chip comprising a processor that processes sensor data, a memory element coupled to the processor, a radio transceiver coupled to the processor that directs communication between the patch-ASIC chip and the base-ASIC chip, and power management circuits for coordinating power dissipation on the gate-ASIC chip;
(e) transmitting said data received in (d) from said gate-ASIC chip to said base-ASIC chip, wherein the base-ASIC chip comprises a processor that processes sensor data, a memory element coupled to the processor, a radio comprising a UWB receiver and a narrowband transmitter coupled to the memory element that transmits said instructions to the patch-ASIC chip and/or the gate-ASIC chip via the narrowband transmitter and receives said data from said patch-ASIC chip and/or said gate-ASIC chip via the UWB receiver, power management circuits for coordinating power dissipation on the base-ASIC chip;
(f) receiving at said base-ASIC chip said data transmitted in (e);
(g) coordinating a function on the patch-ASIC chip and/or gate-ASIC chip by sending instructions from said base-ASIC chip to the patch-ASIC chip and/or the gate-ASIC chip; and,
(h) sending said data from the base-ASIC chip to a host device through a host interface,
wherein the base-ASIC chip consumes more power than the patch-ASIC chip.

18. The method of claim 17 wherein the base-ASIC chip is incorporated into a µ-Base, the patch-ASIC chip is incorporated into a µ-Patch, and the gate-ASIC chip is incorporated into a µ-Gate; wherein each of the µ-Base, µ-Patch, and µ-Gate comprise a printed circuit board and an antenna attached to the printed circuit board for transmitting and receiving radio signals.

19. The method of claim 17 wherein the gate-ASIC chip further comprises a sensor interface for receiving signals from sensors, wherein the gate-ASIC is incorporated into a patch.

20. The method of claim 17, wherein the patch-ASIC chip is configured to wirelessly transmit data to the base-ASIC chip and/or gate-ASIC chip for at least about 2 days while measuring a physiological signal from a subject without changing or recharging a battery coupled to the patch-ASIC chip.

21. The method of claim 17, wherein the ratio of power dissipation of the base-ASIC chip to the power dissipation of the patch-ASIC chip is at least about 3:2.

22. A system for monitoring a physiological condition, comprising:
(a) a patch-ASIC chip that is incorporated into a physiological signal monitoring patch, the patch-ASIC chip comprising a sensor, a sensor interface coupled to the sensor, a processor coupled to the sensor interface, a memory element coupled to the processor, a radio comprising an ultra wideband (UWB) transmitter and a narrowband receiver coupled to the memory element, and power management circuits,
wherein the sensor provides data signals,
wherein the power management circuits manage power dissipation on the patch-ASIC chip, and
wherein the UWB transmitter transmits data signals to a base-ASIC chip, wherein said data signals are transmitted through an antenna incorporated into the patch; and
(b) said base-ASIC chip, comprising a processor that processes data signals, a memory element coupled to the processor, a radio comprising an UWB receiver and a narrowband transmitter coupled to the memory element, power management circuits that coordinate power dissipation on the base-ASIC chip, and a host interface through which the base-ASIC chip communicates with a host device,
wherein the UWB receiver receives the data signals at said base-ASIC chip,
wherein the narrowband transmitter sends instructions wirelessly from the base-ASIC chip to the patch-ASIC chip such that the base-ASIC chip coordinates a function of the physiological signal monitoring patch, and such that said narrowband receiver of said path-ASIC chip receives said instructions,
wherein the base-ASIC chip keeps track of the quality of the wireless links between ASIC chips, and sends commands to the patch-ASIC chip and/or gate-ASIC chips to instruct the chips to switch between UWB and narrowband radio or to raise or lower transmit power in order to lower power consumption or to enhance communication quality, and wherein the base-ASIC chip uses more processing resources than the patch-ASIC chip.

23. The system of claim 22 wherein the base-ASIC chip coordinates one or more of the following functions: initialization and link set up, power management, data packet routing, type of transmission radio, radio transmit-power, radio receive-sensitivity, patch operational integrity, audio signal generation, display activation, or a combination thereof.

24. The system of claim 22 wherein the base-ASIC chip utilizes a packet-data protocol for the ASIC chips and coordinates data packet routing.

25. The system of claim 22 wherein the patch-ASIC chip is configured to wirelessly transmit data to the base-ASIC chip and/or gate-ASIC chip for at least about 2 days while measuring a physiological signal from a subject without changing or recharging a battery coupled to the patch-ASIC chip.

26. The system of claim 22 wherein the base-ASIC chip consumes at least 50% more power than the patch-ASIC chip.

27. A system for monitoring a physiological condition, comprising:
(a) a patch-ASIC chip that is incorporated into a physiological signal monitoring patch, the patch-ASIC chip comprising a sensor, a sensor interface coupled to the sensor, a processor coupled to the sensor interface, a memory element coupled to the processor, a radio comprising an ultra wideband (UWB) transmitter and a narrowband receiver coupled to the memory element, and power management circuits,
wherein the sensor provides data signals,
wherein the power management circuits manage power dissipation on the patch-ASIC chip,
wherein the UWB transmitter transmits data signals to a base-ASIC chip, wherein said data signals are transmitted through an antenna incorporated into the patch,
wherein the patch-ASIC chip is authenticated by bringing the physiological signal monitoring patch in proximity of a device comprising the base-ASIC chip; and
(b) said base-ASIC chip, comprising a processor that processes data signals, a memory element coupled to the processor, a radio comprising an UWB receiver and a narrowband transmitter coupled to the memory element, power management circuits that coordinate power dissipation on the base-ASIC chip, and a host interface through which the base-ASIC chip communicates with a host device,
wherein the UWB receiver receives the data signals at said base-ASIC chip,
wherein the narrowband transmitter sends instructions wirelessly from the base-ASIC chip to the patch-ASIC chip such that the base-ASIC chip coordinates a function of the physiological signal monitoring patch, and such that said narrowband receiver of said path-ASIC chip receives said instructions, and
wherein the base-ASIC chip uses more processing resources than the patch-ASIC chip.

28. The system of claim 27 wherein the base-ASIC chip coordinates one or more of the following functions: initialization and link set up, power management, data packet routing, type of transmission radio, radio transmit-power, radio receive-sensitivity, patch operational integrity, audio signal generation, display activation, or a combination thereof.

29. The system of claim 27 wherein the base-ASIC chip utilizes a packet-data protocol for the ASIC chips and coordinates data packet routing.

30. The system of claim 27 wherein the patch-ASIC chip is configured to wirelessly transmit data to the base-ASIC chip and/or gate-ASIC chip for at least about 2 days while measuring a physiological signal from a subject without changing or recharging a battery coupled to the patch-ASIC chip.

31. The system of claim 27 wherein the base-ASIC chip consumes at least 50% more power than the patch-ASIC chip.

* * * * *

UNITED STATES PATENT AND TRADEMARK OFFICE
CERTIFICATE OF CORRECTION

Page 1 of 1

PATENT NO. : 8,926,509 B2
APPLICATION NO. : 12/134151
DATED : January 6, 2015
INVENTOR(S) : Surendar Magar et al.

It is certified that error appears in the above-identified patent and that said Letters Patent is hereby corrected as shown below:

In the Claims:

Column 45, Line 25, Claim 2, should read --µ-Base-- instead of "Base".

Signed and Sealed this
Twelfth Day of January, 2016

Michelle K. Lee
*Director of the United States Patent and Trademark Office*